United States Patent
Xu et al.

(10) Patent No.: US 12,372,506 B2
(45) Date of Patent: Jul. 29, 2025

(54) MEMS GAS SENSOR, ARRAY THEREOF AND PREPARATION METHOD THEREFOR

(71) Applicant: Wiinaa Co., Ltd., Anhui (CN)

(72) Inventors: Lei Xu, Anhui (CN); Dongcheng Xie, Anhui (CN); Dongliang Chen, Anhui (CN)

(73) Assignee: Wiinaa Co., Ltd., Anhui (CN)

( * ) Notice: Subject to any disclaimer, the term of this patent is extended or adjusted under 35 U.S.C. 154(b) by 389 days.

(21) Appl. No.: 17/913,095

(22) PCT Filed: Jul. 10, 2020

(86) PCT No.: PCT/CN2020/101423
§ 371 (c)(1),
(2) Date: Sep. 20, 2022

(87) PCT Pub. No.: WO2021/189719
PCT Pub. Date: Sep. 30, 2021

(65) Prior Publication Data
US 2023/0204554 A1    Jun. 29, 2023

(30) Foreign Application Priority Data
Mar. 26, 2020 (CN) .......................... 202010222310.3

(51) Int. Cl.
*B81B 7/04* (2006.01)
*G01N 33/00* (2006.01)

(52) U.S. Cl.
CPC ........... *G01N 33/0031* (2013.01); *B81B 7/04* (2013.01); *G01N 33/0073* (2013.01); *B81B 2201/0214* (2013.01)

(58) Field of Classification Search
CPC .............. B81B 2201/0214; B81B 7/04; G01N 33/0073
See application file for complete search history.

(56) References Cited

U.S. PATENT DOCUMENTS

| 5,019,885 A | 5/1991 | Yagawara et al. |
| 9,417,202 B2 | 8/2016 | Park et al. |
| (Continued) | | |

FOREIGN PATENT DOCUMENTS

| CN | 1178903 A | 4/1998 |
| CN | 1684285 A | 10/2005 |
| (Continued) | | |

OTHER PUBLICATIONS

First Office Action for Japanese Application No. 2023-500116, dated Oct. 10, 2023, 18 Pages including English Translation.
(Continued)

*Primary Examiner* — Jamel E Williams
(74) *Attorney, Agent, or Firm* — BROOKS KUSHMAN P.C.

(57) ABSTRACT

A MEMS gas sensor (A), array thereof, and preparation method therefor. The MEMS gas sensor comprises a first substrate (A2) provided with a first cavity (A1), and N gas detection assemblies (A3) provided at an opening of A1, each A3 comprises: a supporting arm (A31) and a gas detection part (A32) provided on the A31; the A32 comprises a strip-shaped heating electrode part (A321), an insulating layer (A322), a strip-shaped detection electrode part (A323), and a gas-sensitive material part (A324) that are stacked sequentially; the A323 comprises a first detection electrode part (A323-1) and a second detection electrode part (A323-2) with a first opening (A325) therebetween; the A324 is provided at the A325; a first end of the A324 is connected to the A323-1, a second end of the A324 is connected to the A323-2; strip-shaped heating electrode parts in each A3 are connected sequentially to form a heater (A8).

14 Claims, 15 Drawing Sheets

(56) References Cited

U.S. PATENT DOCUMENTS

| | | | |
|---|---|---|---|
| 2015/0285754 | A1 | 10/2015 | Park et al. |
| 2015/0285772 | A1* | 10/2015 | Park ..................... G01N 27/123 73/31.05 |
| 2020/0003718 | A1 | 1/2020 | Bartsch et al. |
| 2020/0333277 | A1 | 10/2020 | Xu et al. |

FOREIGN PATENT DOCUMENTS

| | | | |
|---|---|---|---|
| CN | 201141848 | Y | 10/2008 |
| CN | 101329291 | A | 12/2008 |
| CN | 107643326 | A | 1/2018 |
| CN | 108362740 | A | 8/2018 |
| CN | 208109742 | U | 11/2018 |
| CN | 111272828 | A | 6/2020 |
| EP | 2930500 | A1 | 10/2015 |
| JP | 2004037180 | A | 2/2004 |
| JP | 2014153135 | A | 8/2014 |
| JP | 2015200644 | A | 11/2015 |
| JP | 2017090188 | A | 5/2017 |
| KR | 20050051884 | A | 6/2005 |
| KR | 20050097421 | A * | 10/2005 |
| KR | 100609764 | B1 * | 8/2006 |
| KR | 20110108527 | A | 10/2011 |
| KR | 20190014981 | A | 2/2019 |

OTHER PUBLICATIONS

Supplementary European Search Report, Prepared by the European Patent Office for EP 20 92 6979, Date Jun. 6, 2023.

Examination Report, prepared by the Intellectual Property India, Date Dec. 12, 2022.

The first office action with English translation 202010222310.3, prepared by the China National Intellectual Property Administration, dated Apr. 19, 2021, 20 pages with English translation.

The second office action with English translation 202010222310.3, prepared by the China National Intellectual Property Administration, dated Aug. 24, 2021, 15 pages with English translation.

The third office action with English translation 202010222310.3, prepared by the China National Intellectual Property Administration, dated Dec. 21, 2021, 11 pages with English translation.

International Search report for PCT/CN2020/101423, prepared by the China National Intellectual Property Administration, mailing date Dec. 25, 2020, 7 pages including the English Translation.

* cited by examiner

A325
A323-1    A323-2
FIG. 4J
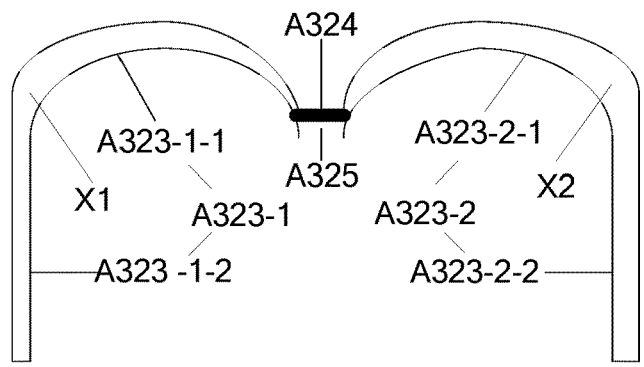
FIG. 5
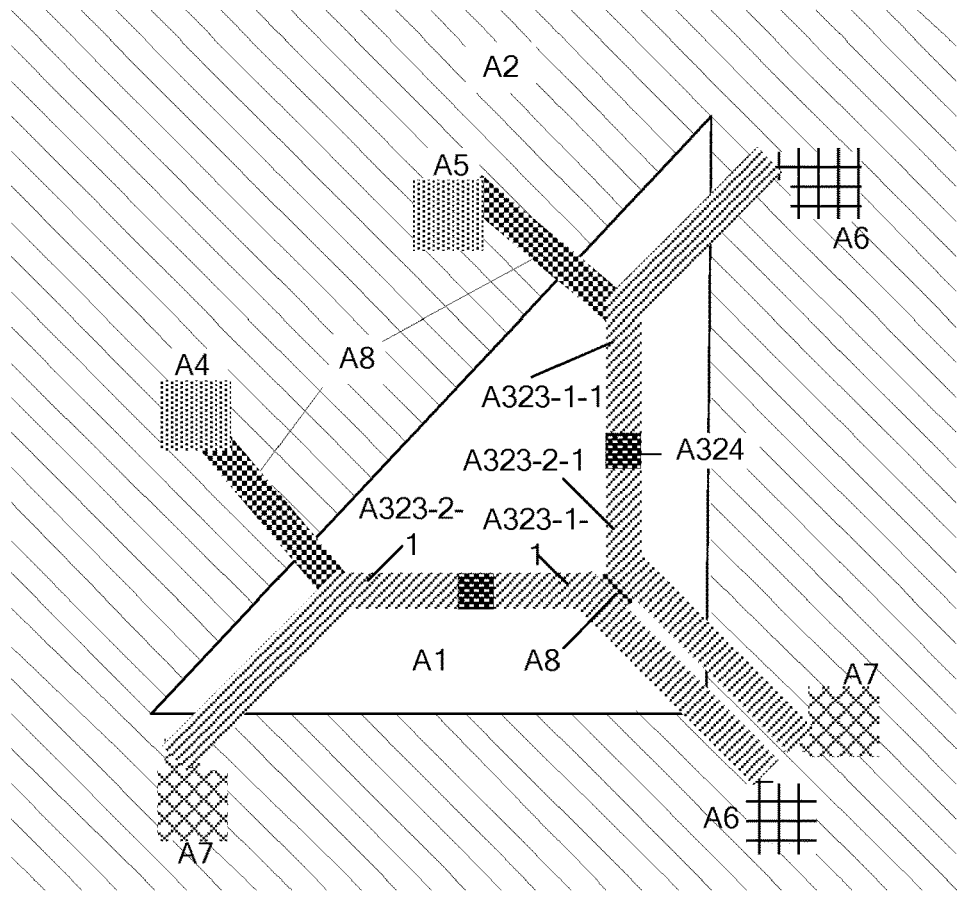
FIG. 6

MEMS GAS SENSOR, ARRAY THEREOF AND PREPARATION METHOD THEREFOR

CROSS-REFERENCE TO RELATED APPLICATIONS

The present application is a U.S. National Phase Entry of International Application No. PCT/CN2020/101423 having an international filing date of Jul. 10, 2020, which claims priority to the Chinese Patent Application No. 202010222310.3, entitled "MEMS Gas Sensor, Array thereof and Preparation Method therefor", and filed to the CNIPA on Mar. 26, 2020. The above-identified applications are incorporated into this present application herein by reference in their entirety.

TECHNICAL FIELD

The present application relates to, but is not limited to, the field of gas detection technologies, in particular to a Micro-Electro-Mechanical System (MEMS) gas sensor, an array thereof and a manufacturing method therefor.

BACKGROUND

Odor recognition is one of the important application fields of gas sensors. Metal-oxide semiconductor gas sensors are widely used in odor recognition devices for their excellent characteristics such as low power consumption, low cost, high integration and good response to various gases. Metal-Oxide Semiconductor (MOS) type Micro-Electro-Mechanical System (MEMS) gas sensors are researched mainly based on gas sensors of closed film type and gas sensors of suspended film type. The former has higher mechanical strength, while the latter has faster thermal response speed. However, the above types of gas sensors still have a problem of large power consumption.

SUMMARY

The following is a summary of the subject matter described in detail herein. This summary is not intended to limit the protection scope of the claims.

Embodiments of the present disclosure provide an MEMS gas sensor, an array thereof and a manufacturing method therefor.

In one aspect, a Micro-Electro-Mechanical System (MEMS) gas sensor A is provided in an embodiment of the present disclosure. The MEMS gas sensor may include a first substrate provided with a first surface on which a first cavity is provided, N gas detection components disposed at an opening of the first cavity; wherein N is a positive integer greater than or equal to 2.

Each gas detection component includes a support arm and a gas detection part disposed on the support arm, the gas detection part includes a strip-shaped heating electrode part, an insulating layer, a strip-shaped detection electrode part and a gas sensitive material part, that are sequentially stacked, wherein the strip-shaped detection electrode part includes a first detection electrode part and a second detection electrode part, a first opening is provided between the first detection electrode part and the second detection electrode part, the gas sensitive material part is disposed at a position of the first opening, a first end of the gas sensitive material part is connected with the first detection electrode part, and a second end of the gas sensitive material part is connected with the second detection electrode part. Strip-shaped heating electrode parts in all gas detection components are sequentially connected to form a heater.

In another aspect, an MEMS gas sensor array is further provided in an embodiment of the present disclosure, the gas sensor array may include the MEMS gas sensor of any of the above-mentioned embodiments.

In yet another aspect, a method for manufacturing an MEMS gas sensor is further provided in an embodiment of the present disclosure, and the MEMS gas sensor is the MEMS gas sensor described in any one of the above-mentioned embodiments. The method may include: preparing a first substrate; and manufacturing N gas detection components on a first surface of the first substrate, wherein N is a positive integer greater than or equal to 2, and the gas detection component includes a support arm and a gas detection part disposed on the support arm, the gas detection part includes a strip-shaped heating electrode part, an insulating layer, a strip-shaped detection electrode part and a gas sensitive material part, that are sequentially stacked, wherein the strip-shaped detection electrode part includes a first detection electrode part and a second detection electrode part, a first opening is provided between the first detection electrode part and the second detection electrode part, the gas sensitive material part is disposed at a position of the first opening, a first end of the gas sensitive material part is connected with the first detection electrode part, and a second end of the gas sensitive material part is connected with the second detection electrode part; strip-shaped heating electrode parts in all gas detection components are sequentially connected to form a heater.

Other aspects will become apparent after reading and understanding the drawings and detailed description.

BRIEF DESCRIPTION OF DRAWINGS

FIG. 4J is a schematic diagram of a tenth shape formed by a first detection electrode part and a second detection electrode part according to an exemplary embodiment of the present disclosure.

FIG. 5 is a schematic diagram of a structure of an m-shaped gas detection component according to an exemplary embodiment of the present disclosure.

FIG. 6 is a schematic diagram of a structure of a V-shaped MEMS gas sensor constituted by two pairs of first detection electrode segments and third detection electrode segments according to an exemplary embodiment of the present disclosure.

DETAILED DESCRIPTION

Multiple embodiments are described herein, and the description is exemplary and unrestrictive. Unless specifically limited, any feature or element in any embodiment may be used in combination with, or in place of, any other feature or element in any other embodiment.

Figure 1:
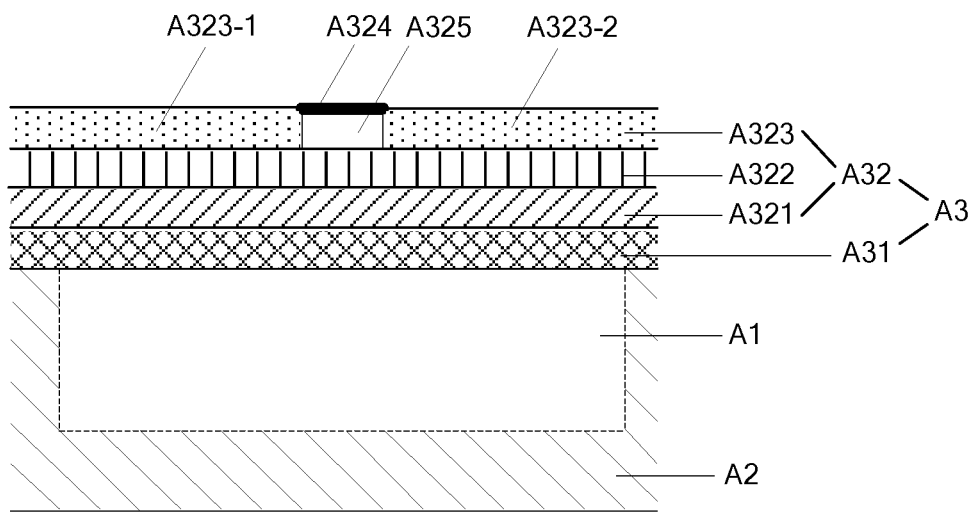
FIG. 1 is a cross-sectional view of an MEMS gas sensor cavity portion according to an exemplary embodiment of the present disclosure.
Figure 2:
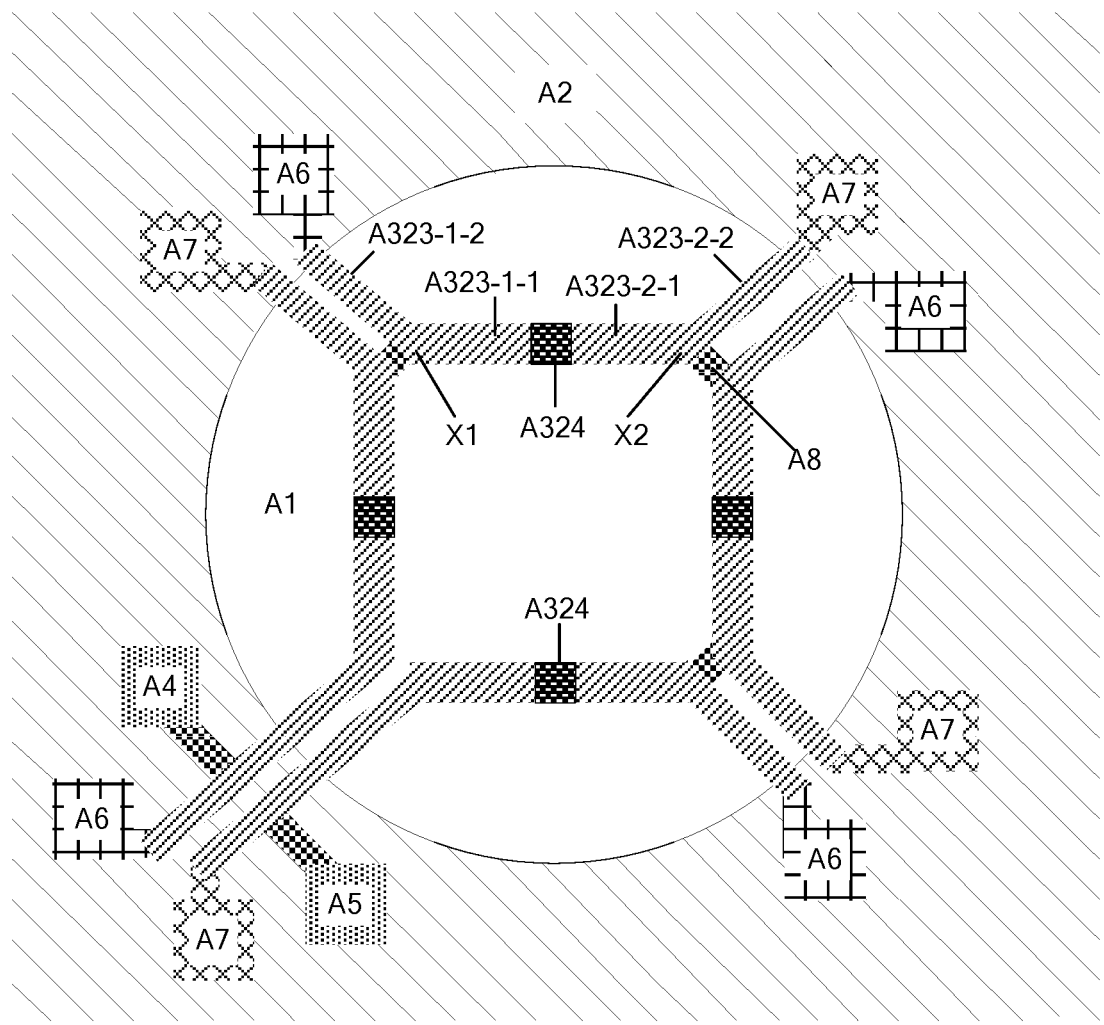
FIG. 2 is a top view of an MEMS gas sensor according to an exemplary embodiment of the present disclosure.

In an exemplary embodiment, a Micro-Electro-Mechanical System (MEMS) gas sensor A is provided. As shown in FIGS. 1 and 2, the MEMS gas sensor A may include a first substrate A2 with a first surface on which a first cavity A1 is provided, N gas detection components A3 disposed at an opening of the first cavity; wherein N is a positive integer greater than or equal to 2.

Each gas detection component A3 may include a support arm A31 and a gas detection part A32 disposed on the support arm A31. The gas detection part A32 may include a strip-shaped heating electrode part A321, an insulating layer A322, a strip-shaped detection electrode part A323, and a gas sensitive material part A324, that are sequentially stacked. The strip-shaped detection electrode part A323 may include a first detection electrode part A323-1 and a second detection electrode part A323-2. A first opening A325 is provided between the first detection electrode part A323-1 and the second detection electrode part A323-2, the gas sensitive material part A324 is disposed at a position of the first opening A235, a first end of the gas sensitive material part A324 is connected with the first detection electrode part A323-1, and a second end of the gas sensitive material part A324 is connected with the second detection electrode part A323-2.

Strip-shaped heating electrode parts A321 in all gas detection components A3 are sequentially connected to form a heater A8.

In an exemplary embodiment, the strip-shaped heating electrode parts A321 in the all gas detection components A3 are sequentially connected to form a heater A8, which means that N strip-shaped heating electrode parts A321 in the N gas detection components A3 are jointly connected to form a heater, including any of the following cases.

In case 1, one or more cavities are provided on the first surface of the first substrate A2, wherein at least one cavity is the first cavity A1, and strip-shaped heating electrode parts A321 in the N gas detection components A3 in the first cavity A1 are sequentially connected to form a heater A8.

In case 2, multiple first cavities are provided on the first surface of the first substrate A2, wherein strip-shaped heating electrode parts A321 in all of gas detection components A3 in a part or all of the first cavities A1 are sequentially connected to form a heater A8.

The sequential connection may be sequential connection based on a positional relationship, i.e., strip-shaped heating electrode parts in adjacent gas detection components are connected together, without excluding a case in which the connection is made based on a non-positional relationship.

In an exemplary embodiment, the gas detection parts A32 in the N gas detection components A3 may be symmetrically disposed.

In an exemplary embodiment, the strip-shaped detection electrode part A323 may include a first detection electrode part A323-1 and a second detection electrode part A323-2. A first opening A325 is provided between the first detection electrode part A323-1 and the second detection electrode part A323-2, the gas sensitive material part A324 is disposed at a position of the first opening A235, a first end of the gas sensitive material part A324 is connected with the first detection electrode part A323-1, and a second end of the gas sensitive material part A324 is connected with the second detection electrode part A323-2.

In an exemplary embodiment, the support arm A31 may be a part of a support film formed on the first substrate A2, that is, the support film is mounted at an area where the opening of the first cavity is located.

In an exemplary embodiment, the first cavity A1 provided on the first surface of the first substrate A2 may include one or more first cavities, multiplethe gas detection component A3 provided at the opening of each first cavity A1 may be multiple gas detection components A3, and multiplethe support arm A31 mounted on each first cavity A1 may be multiple the support arms A31, correspondingly. The number of the first cavities A1 and the number of the support arms A31 are not limited herein.

In an exemplary embodiment, the multiple gas detection components A3 may be disposed symmetrically or asymmetrically. Each gas detection component A3 itself may be symmetrical or asymmetrical.

In the exemplary embodiments herein, there are no limitations on a size, shape and formation position of the first cavity A1.

In the exemplary embodiments herein, there is no limitation on a size (e.g. width) of the support arm A31.

The MEMS gas sensor according to the exemplary embodiments of the present disclosure is manufactured by using an MEMS process to achieve manufacturing and packaging of the sensor in a single process. A mass manufacturing process of gas sensors can be significantly simplified, a cost thereof can be greatly reduced, an efficiency thereof can be improved, and a manufacturing cycle thereof can be shortened, which can be beneficial to improving the consistency and stability of the sensors. An effective area of the sensor is manufactured on the strip-shaped support arm with a strip-shaped support arm structure, which omits a heater structure with a serpentine winding, spiral winding or folded winding and an interdigital electrode structure, such that the power consumption and thermal response time of the gas sensor can be greatly reduced. Particularly, when the gas detection parts A32 on the N strip-shaped support arms are symmetrically disposed, a thermal response speed can be improved, thereby the power consumption can be reduced. When the N support arms in the gas detection components form a stable polygon, after the heating electrode part is powered on, especially when the gas sensitive material requires to be heated to a higher temperature, better support and stability can be ensured, and structural deformation, which affects the thermal response speed and is caused by high temperature, can be avoided. In addition, since the N strip-shaped heating electrode parts share one closed-loop heater, (N−1) heaters are reduced, so that heat taken away from the wire of the heater is reduced, and the power consumption is reduced, the area occupied by the heater can be effectively reduced, which can improve the integration level of the gas sensor.

In an exemplary embodiment, the MEMS gas sensor A may further include a first heating electrode pin A4 and a second heating electrode pin A5, that are disposed on the first substrate A2.

The first heating electrode pin A4 is connected with a first end of the heater A8, and the second heating electrode pin A5 is connected with a second end of the heater A8, to form a heating circuit.

In an exemplary embodiment, the MEMS gas sensor A may further include one or N first detection electrode pins A6 and one or N second detection electrode pins A7, that are disposed on the first substrate A2.

A first end of the first detection electrode part A323-1 is connected with the first end of the gas sensitive material part A324, and a second end of the first detection electrode part A323-1 is connected with one first detection electrode pin A6; a first end of the second detection electrode part A323-2 is connected with the second end of the gas sensitive material part A324, and a second end of the second detection electrode part A323-2 is connected with one second detection electrode pin A7, to form a detection circuit. In other words, a first end of a first detection electrode part is connected with a first end of a gas sensitive material part, a second end of the first detection electrode part is connected with a first detection electrode pin, a first end of a second detection electrode part is connected with a second end of a gas sensitive material part, and a second end of the second detection electrode part is connected with a second detection electrode pin.

In an exemplary embodiment, as shown in FIG. 2, the N gas detection components A3 may include N pairs of detection electrode pins, wherein each pair of detection electrode pins include a first detection electrode pin A6 and a second detection electrode pin A7. The N pairs of detection electrode pins are referred to as N pairs of first detection electrode pins A6 and second detection electrode pins A7 hereinafter.

The N pairs of first detection electrode pins A6 and second detection electrode pins A7 are connected, respectively, to the first detection electrode parts A323-1 and the second detection electrode parts A323-2 in the N gas detection components A3. For example, the first detection electrode pins A6 are connected with the first detection electrode parts A323-1, and the second detection electrode pins A7 are connected with the second detection electrode parts A323-2.

In an exemplary embodiment, each gas detection part A32 may be correspondingly provided with a pair of detection electrode pins, including a first detection electrode pin A6 and a second detection electrode pin A7. One of the first detection electrode pin A6 and the second detection electrode pin A7 may be a ground pin, and the other one may be a voltage pin. Alternatively, one of the first detection electrode pin A6 and the second detection electrode pin A7 is a positive pin, and the other one is a negative pin.

Figure 3:
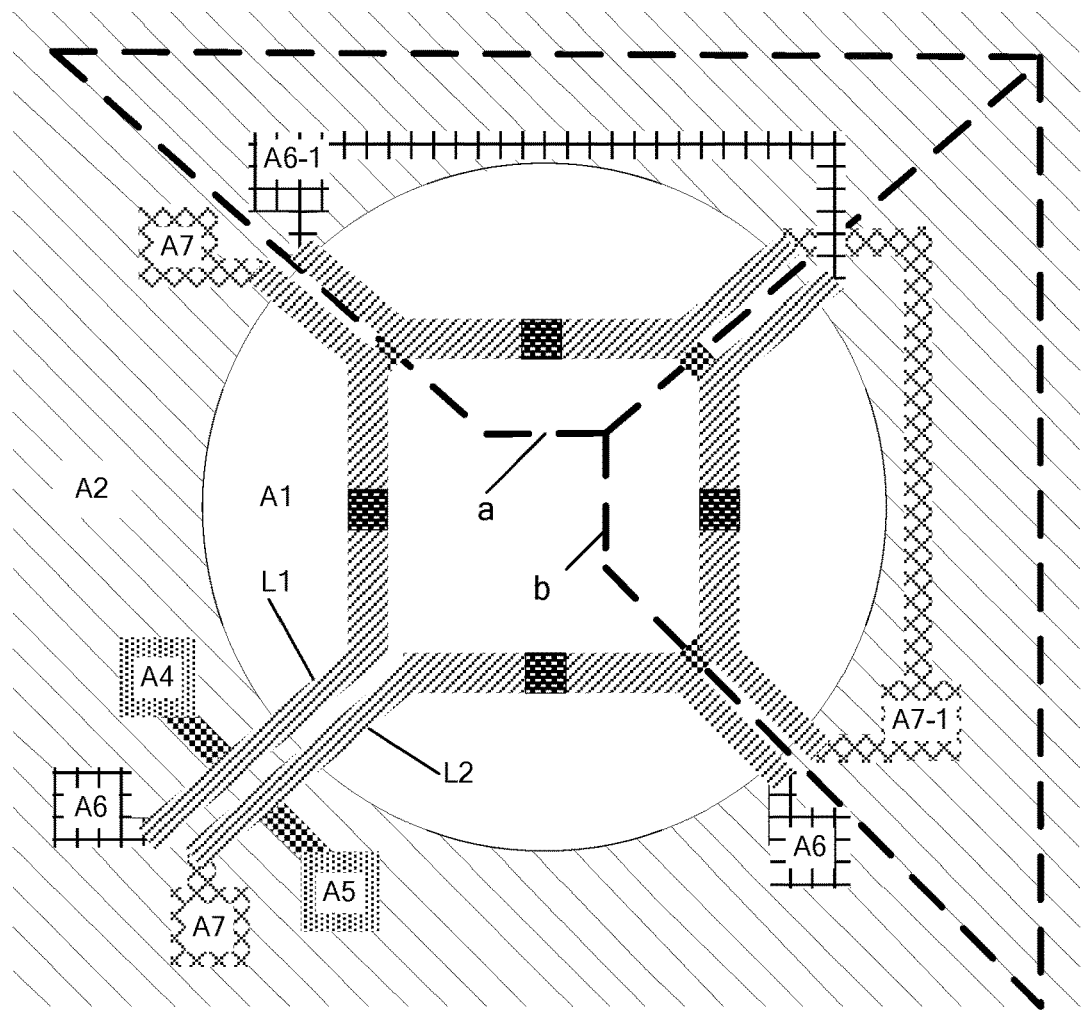
FIG. 3 is a schematic diagram of a structure of strip-shaped detection electrode parts in two gas detection components sharing a pair of first detection electrode pin and second detection electrode pin according to an exemplary embodiment of the present disclosure.

In an exemplary embodiment, any multiple strip-shaped detection electrode parts A323 of all strip-shaped detection electrode parts A323 provided at the opening of a first cavity A1 may share one pair of first detection electrode pin A6 and second detection electrode pin A7, that is, second ends of the multiple first detection electrode parts are connected with one first detection electrode pin; and/or, second ends of the multiple second detection electrode parts are connected with one second detection electrode pin. As shown in FIG. 3, it shows an embodiment in which strip-shaped detection electrode parts A323 in two gas detection components share a pair of first detection electrode pin A6 and second detection electrode pin A7. The strip-shaped detection electrode parts A323 in the two gas detection components selected by dashed line boxes a and b in FIG. 3 share the first detection electrode pin A6-1 and the second detection electrode pin A7-1 (when the A6-1 and A7-1 are actually formed, an isolation film may be provided in an area where the two pins intersect). The pin connection mode in FIG. 3 is only taken as an example, and the pins are used to connect with external circuits. The strip-shaped detection electrode parts and the detection electrode pins may be directly connected or connected through leads. In an exemplary embodiment, one or more sets of strip-shaped detection electrode parts A323 in all strip-shaped detection electrode parts A323 provided at the opening of one first cavity A1 may share a pair of first detection electrode pin A6 and second detection electrode pin A7, and at least one strip-shaped detection electrode part A323, that does not share the first detection electrode pin A6 and the second detection electrode pin A7 with other strip-shaped detection electrode parts A323, may be included.

Figure 7A:
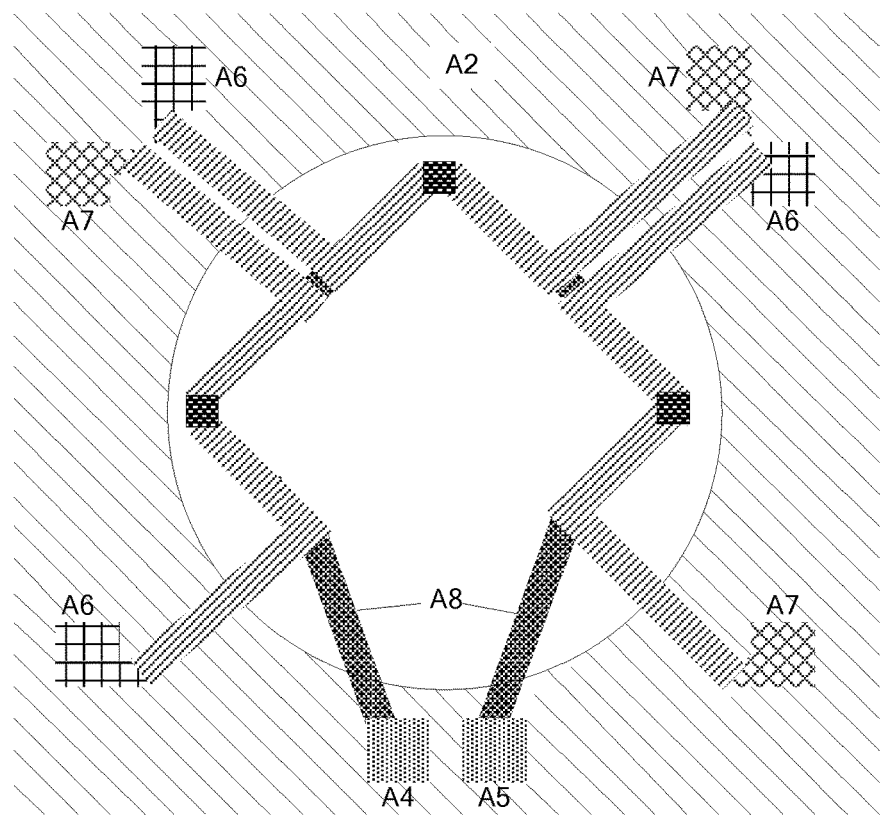
FIG. 7A is a schematic diagram of a structure of the first shape being an annular sawtooth according to an exemplary embodiment of the present disclosure.

The heater may include a heating part located below the detection electrode part and a lead-out part connected with the heating electrode pins, wherein the lead-out part may share a support arm with the detection electrode part, as shown in FIGS. 2 and 3, or the lead-out part may have its own support arm, as shown in FIGS. 6 and 7A. The heater is divided into the heating part and the lead-out part for convenience only, and both of the heating part and the lead-out part are the aforementioned heating electrode part. In the example shown in FIG. 3, the lead-out part of the heater and the detection electrode part share a first support arm L1 and a second support arm L2, wherein the first support arm L1 and the second support arm L2 may be independently disposed, that is, a width of each support arm is equal to or slightly larger than a width of the strip-shaped detection electrode part and the strip-shaped heating electrode part supported thereon. In another embodiment, the first support arm L1 and the second support arm L2 may be integrated together, that is, the support film portion between the first support arm L1 and the second support arm L2 is not etched during manufacturing.

In an exemplary embodiment, strip-shaped detection electrode parts A323 sharing the first detection electrode pin A6 and the second detection electrode pin A7, and strip-shaped detection electrode parts A323 that do not share the first detection electrode pin A6 and the second detection electrode pin A7 may be combined respectively to be symmetrically arranged (for example, multiple strip-shaped detection electrode parts A323 that share the first detection electrode pin A6 and the second detection electrode pin A7 are combined in a symmetrical shape, while multiple strip-shaped detection electrode parts A323 that do not share the first detection electrode pin A6 and the second detection electrode pin A7 are combined in a symmetrical shape), or may be combined together to be arranged symmetrically (for example, multiple strip-shaped detection electrode parts A323 that share the first detection electrode pin A6 and the second detection electrode pin A7, and multiple strip-shaped detection electrode parts A323 that do not share the first detection electrode pin A6 and the second detection electrode pin A7 are arranged together to form a symmetrical shape).

In an exemplary embodiment, the strip-shaped detection electrode parts A323 in the gas detection components on the multiple the support arms A31 mounted at the opening of the first cavity A1 may share a heater, so that the first cavity A1 may employ a pair of heating electrode pins, including a first heating electrode pin A4 and a second heating electrode pin A5. One of the first heating electrode pin A4 and the second heating electrode pin A5 may be a ground pin, and the other one may be a voltage pin. Alternatively, one of the first detection electrode pin A6 and the second detection electrode pin A7 is a positive pin, and the other one is a negative pin.

In an exemplary embodiment, each gas detection component A3 itself may be symmetrical, for example, the first detection electrode part A323-1 and the second detection electrode part A323-2 are symmetrical to each other, and the first opening A325 may be located at the symmetry axis (position of the symmetry axis) of the first detection electrode part A323-1 and the second detection electrode part A323-2.

In an exemplary embodiment, the first detection electrode part A323-1 and the second detection electrode part A323-2 may also be disposed asymmetrically.

In an exemplary embodiment, as shown in FIGS. 4A, 4B, 4C, 4D, 4E, 4F, 4G, 4H, 4I, and 4J, a symmetrical shape formed by the first detection electrode part A323-1 and the second detection electrode part A323-2 may include, but is not limited to, any one or more of the followings: a symmetrical geometry, a symmetrical character shape, a symmetrical pattern, and any symmetrical irregular shape.

Figure 4A:
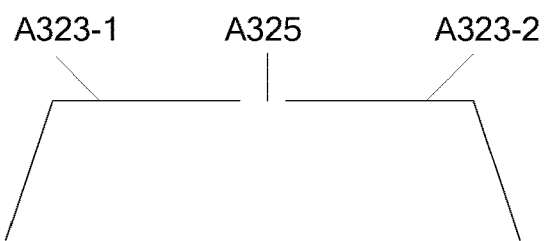
FIG. 4A is a schematic diagram of a first shape formed by a first detection electrode part and a second detection electrode part according to an exemplary embodiment of the present disclosure.
Figure 4B:
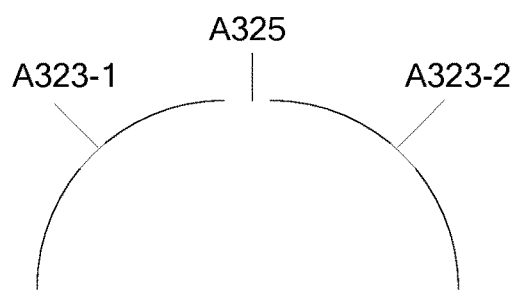
FIG. 4B is a schematic diagram of a second shape formed by a first detection electrode part and a second detection electrode part according to an exemplary embodiment of the present disclosure.
Figure 4C:
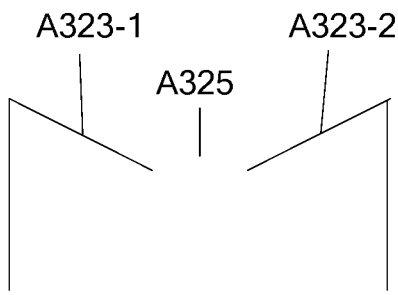
FIG. 4C is a schematic diagram of a third shape formed by a first detection electrode part and a second detection electrode part according to an exemplary embodiment of the present disclosure.
Figure 4D:
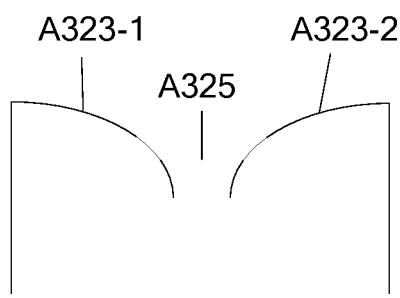
FIG. 4D is a schematic diagram of a fourth shape formed by a first detection electrode part and a second detection electrode part according to an exemplary embodiment of the present disclosure.
Figure 4E:
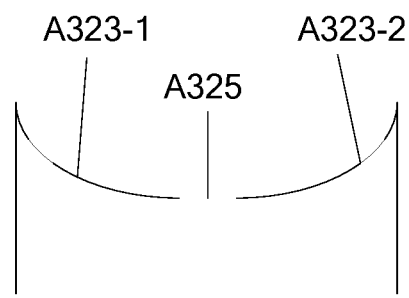
FIG. 4E is a schematic diagram of a fifth shape formed by a first detection electrode part and a second detection electrode part according to an exemplary embodiment of the present disclosure.
Figure 4F:
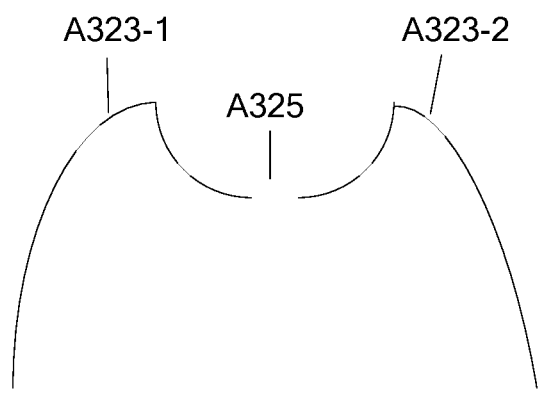
FIG. 4F is a schematic diagram of a sixth shape formed by a first detection electrode part and a second detection electrode part according to an exemplary embodiment of the present disclosure.
Figure 4G:
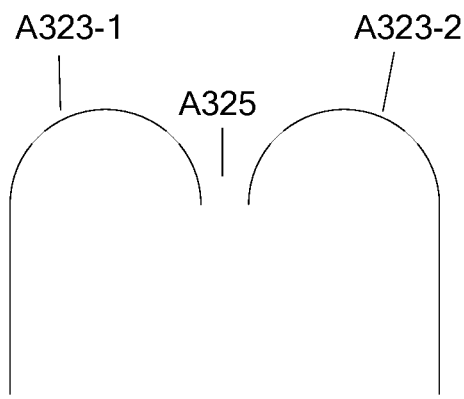
FIG. 4G is a schematic diagram of a seventh shape formed by a first detection electrode part and a second detection electrode part according to an exemplary embodiment of the present disclosure.
Figure 4H:
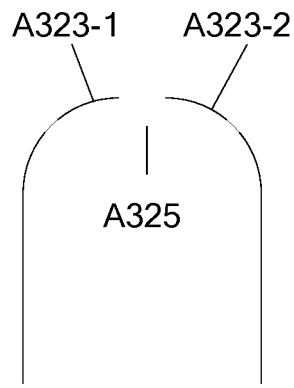
FIG. 4H is a schematic diagram of an eighth shape formed by a first detection electrode part and a second detection electrode part according to an exemplary embodiment of the present 5 disclosure.
Figure 4I:
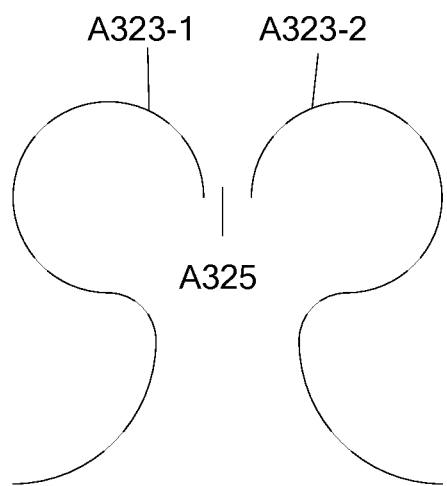
FIG. 4I is a schematic diagram of a ninth shape formed by a first detection electrode part and a second detection electrode part according to an exemplary embodiment of the present disclosure.

In an exemplary embodiment, for example, the first detection electrode part A323-1 and the second detection electrode part A323-2 may constitute a symmetrical arc, and the first opening A325 may be located at a vertex of the arc. For example, the first detection electrode part A323-1 and the second detection electrode part A323-2 may constitute a semicircle, a A shape or the like, and the first opening A325 may be located at a vertex of the semicircle or of the A shape, as shown in FIGS. 4B and 4J. The vertex refers to an intersection of the line and a symmetry axis of the line, for example, the vertex of the arc refers to an intersection of the symmetry axis of the arc and the arc.

In an exemplary embodiment, for example, the first detection electrode part A323-1 and the second detection electrode part A323-2 may constitute a symmetrical trapezoid, rectangle, square or the like, without a lower bottom, and the first opening A325 may be located at the middle of an upper bottom of the symmetrical trapezoid, rectangle, square, etc. FIG. 4A shows an embodiment in which the first detection electrode part A323-1 and the second detection electrode part A323-2 constitute a symmetrical trapezoid without a lower bottom.

In an exemplary embodiment, for example, the first detection electrode part A323-1 and the second detection electrode part A323-2 may constitute a symmetrical character shape, and the first opening A325 may be located at a symmetrical point or a vertex of a symmetrical line position (i.e., an intersection of the symmetrical axis of the character shape and the character shape) of the character shape itself. For example, the first detection electrode part A323-1 and the second detection electrode part A323-2 may constitute an m shape, n shape, M shape or the like, and the position of the first opening A325 in the m shape, n shape, or M shape may be that shown in FIGS. 4G, 4H, and 4C. FIGS. 4D, 4E, 4F, and 4I show variations of the M shape, the shapes given herein are taken as an example only, and in other embodiments, other variations may be possible.

In an exemplary embodiment, as shown in FIGS. 2 and 5, when the first detection electrode part A323-1 and the second detection electrode part A323-2 may constitute a symmetrical geometry (such as the symmetrical trapezoid, or the equilateral trapezoid) or a symmetrical character shape (such as the M shape), the first detection electrode part A323-1 and the second detection electrode part A323-2 may have the following characteristics: the first detection electrode part A323-1 may include a first bending point X1 at which the first detection electrode part A323-1 is bent, and at which the first detection electrode part A323-1 is divided into a first detection electrode segment A323-1-1 and a second detection electrode segment A323-1-2; the second detection electrode part A323-2 may include a second bending point X2 at which the second detection electrode part A323-2 is bent, and at which the second detection electrode part A323-2 is divided into a third detection electrode segment A323-2-1 and a fourth detection electrode segment A323-2-2; wherein, the first opening A325 is disposed between the first detection electrode segment A323-1-1 and the third detection electrode segment A323-2-1, and the first detection electrode segments A323-1-1 and the third detection electrode segments A323-2-1 in the N gas detection components A3 may jointly constitute into a first shape which is a symmetrical shape; as shown in FIG. 2, a first shape constituted by four gas detection components A3 is a square; a strip-shaped heating electrode part A321 in each gas detection component A3 is disposed at a corresponding position of the first detection electrode part A323-1-1 and the third detection electrode part A323-2-1, that is, in an area between the first bending point X1 and the second bending point X2.

In the above-mentioned embodiment, the positions of the bending points are explained by taking the first detection electrode part A323-1 and the second detection electrode part A323-2 which jointly constitute a symmetrical geometry (such as the symmetrical trapezoid, or the equilateral trapezoid) or a symmetrical character shape (such as the n shape, the m shape or the M shape) as an example. In an exemplary embodiment, the positions of the bending points may be asymmetrical, for example, when the first detection electrode part and the second detection electrode part form an asymmetrical geometry or an asymmetrical character shape, the positions of the bending points may not be symmetrical with a midline between the first detection electrode part and the second detection electrode part. In an exemplary embodiment, the detection electrode part may be not significantly bent in shape at the position of the bending point, for example, the bending point may be any point on the arc when the detection electrode part is an arc.

In an exemplary embodiment, the first shape may be constituted by a first detection electrode segment A323-1 and a third detection electrode segment A323-2-1 in any two adjacent gas detection components A3, wherein the first detection electrode segment A323-1-1 and the third detection electrode segment A323-2-1 are close to each other but not connected. For example, in any two adjacent gas detection components A3, the third detection electrode segment A323-2-1 in a first gas detection component is close to the first detection electrode segment A323-1-1 in a second gas detection component, and a distance between the first detection electrode segment A323-1-1 and the third detection electrode segment A323-2-1 may meet a preset distance range. The preset distance range may be defined according to requirements or process conditions, and there is no limited thereon here.

Figure 8:
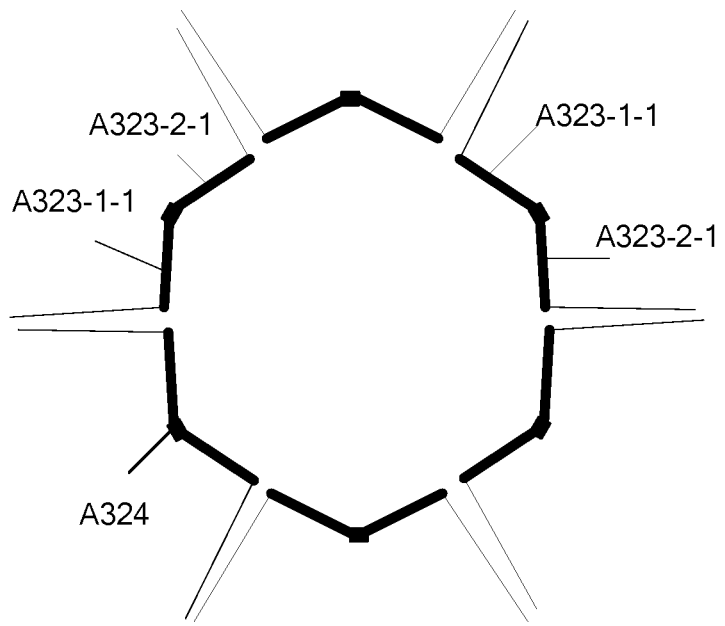
FIG. 8 is a schematic diagram of yet still another structure of the first shape being an annular sawtooth according to an exemplary embodiment of the present disclosure.

In an exemplary embodiment, the first detection electrode segment A323-1-1 and the third detection electrode segment A323-2-1 may constitute a straight line. For example, the first detection electrode segment A323-1-1 and the third detection electrode segment A323-2-1 in a gas detection component may be located in the same straight line, as shown in FIG. 2. Alternatively, in two adjacent gas detection components, the third detection electrode segment in a first gas detection component and the first detection electrode segment in a second gas detection component are in the same straight line, as shown in FIG. 8.

The first shape may include, but is not limited to, a symmetric geometry.

In an exemplary embodiment, when there are two the gas detection components A3, the first shape may be a V shape or an inverted V-shape (Λ), as shown in FIG. 6, a shape constituted by two pairs of first detection electrode segments A323-1-1 and third detection electrode segments A323-2-1 in the two gas detection components is a V shape.

Figure 7B:
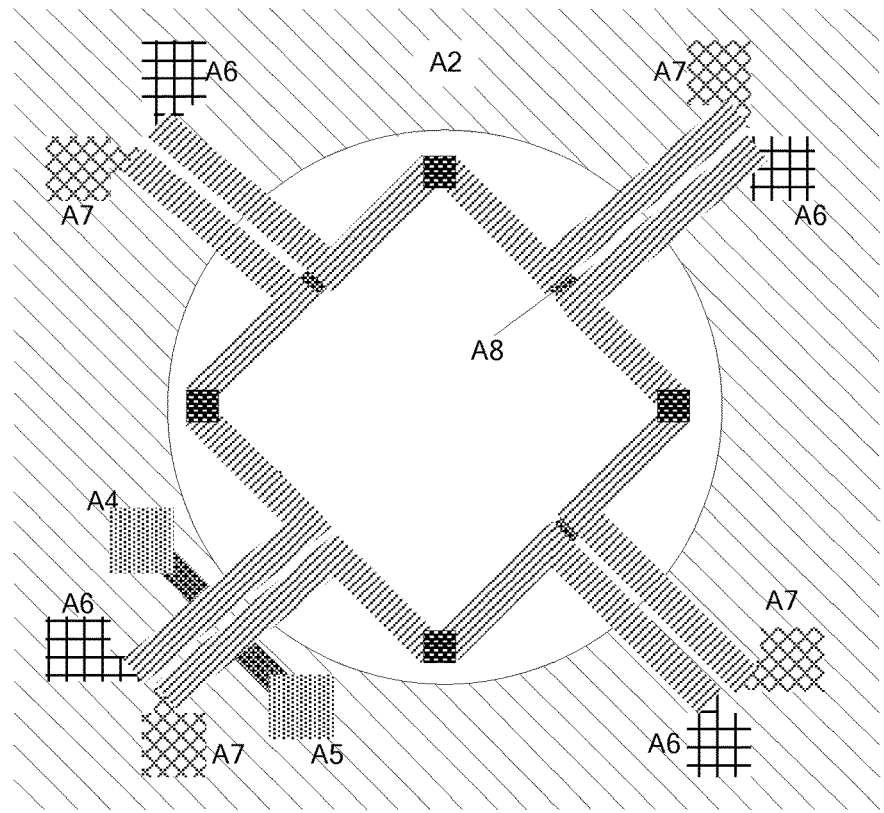
FIG. 7B is a schematic diagram of another structure of the first shape being an annular sawtooth according to an exemplary embodiment of the present disclosure.
Figure 9:
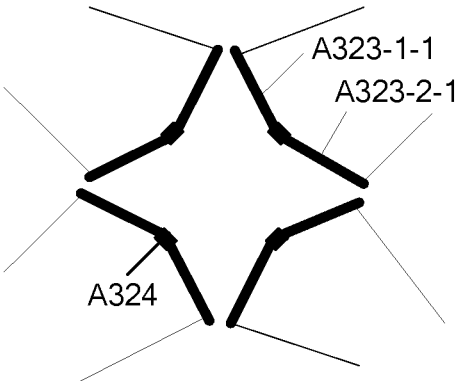
FIG. 9 is a schematic diagram of yet still another yet structure of the first shape being an annular sawtooth according to an exemplary embodiment of the present disclosure.

In an exemplary embodiment, the first shape may be a regular polygon (e.g., a regular triangle, a square, a regular pentagon, a hexagon, etc.) when there are more than two gas detection components A3. For example, in each of the gas detection components A3, the first detection electrode segment A323-1-1 and the third detection electrode segment A323-2-1 may form a V shape or a Λ shape, and the first shape formed by the detection electrode parts of the multiple gas detection components A3 may include, but is not limited to, a regular polygon (as shown by black lines in FIG. 8) or an annular sawtooth. The annular sawtooth is shown, for example, in FIGS. 7 to 9. FIG. 7A shows a sawtooth shape including three teeth, and FIG. 7B shows a sawtooth shape including four teeth. FIG. 8 shows a sawtooth shape including six sawteeth, which approximates a regular hexagon because an angle of each tooth makes a part of each tooth and a part of an adjacent tooth form into an approximate straight line in FIG. 8. FIG. 9 shows an annular sawtooth shape including 4 teeth. The above-mentioned examples are for illustration only, and in other embodiments, the number of teeth in the sawtooth shape and the angle of each tooth may be set as required and are not limited herein.

Figure 10:
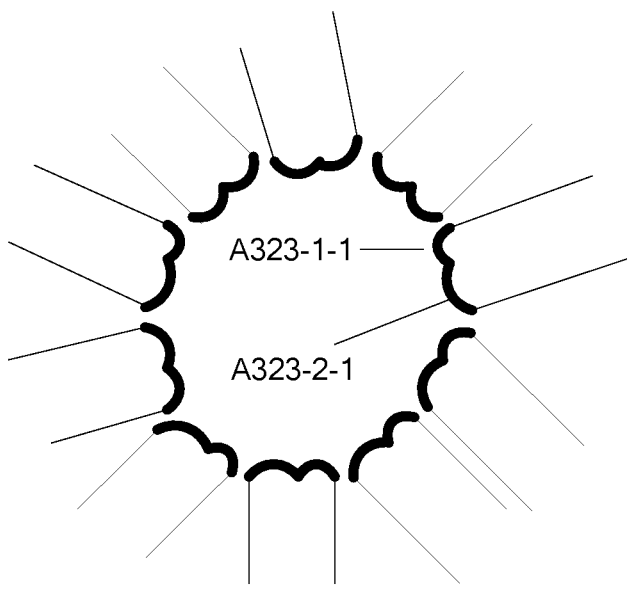
FIG. 10 is a schematic diagram of a first shape constituted by an undulating shape of tops of multiple m shapes according to an exemplary embodiment of the present disclosure.
Figure 11:
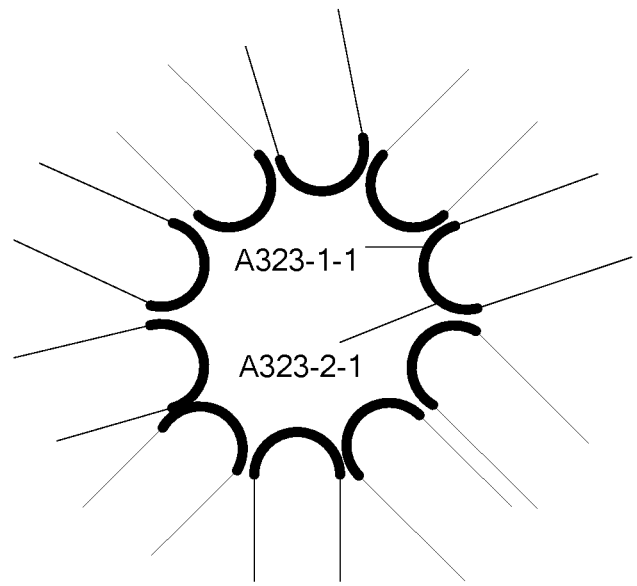
FIG. 11 is a schematic diagram of a first shape constituted by a convex shape at tops of multiple n shapes according to an exemplary embodiment of the present disclosure.
Figure 12:
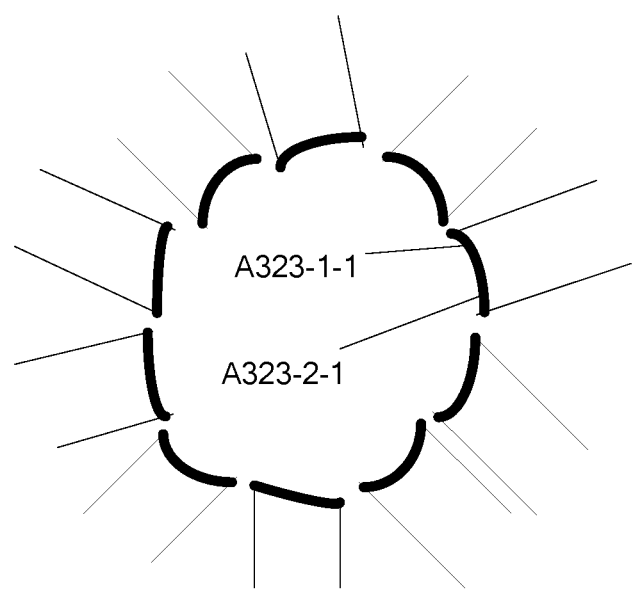
FIG. 12 is a schematic diagram of the first shape constituted by a concave shape at tops of multiple n-like shapes according to an exemplary embodiment of the present disclosure.

In an exemplary embodiment, the first shape may be wavy or approximately circular when there are more than two gas detection components A3. For example, the first detection electrode segment A323-1-1 and the third detection electrode segment A323-2-1 may be combined into an arc (e.g., an undulating shape at a top of an m shape as shown by a black bold line in FIG. 10, or a convex shape at a top of an n shape as shown by a black bold line in FIG. 11), then the first shape may include, but is not limited to, an annular wave. For example, when multiple m (or n) shapes are adjacent in this case, the undulating shapes at the top of the m shapes (or the convex shapes at the top of the n shapes) may be combined in turn to constitute a wave shape, and the wave shape may constitute an annular wave due to its adjacent head and tail. The multiple m and/or n shapes may be rounded or quasi-rounded in order to constitute a symmetrical first shape, so that the wavy shape is rounded or quasi-rounded through adjacent head and tail. For another example, the arc that the first detection electrode segment A323-1-1 and the third detection electrode segment A323-2-1 may form may be an n-like shape. As shown by black bold lines in FIG. 12, a concave shape is provided at a top of the n-like shape. When multiple n-like shapes are adjacent, the concave shapes at the tops of the n-like shapes may be combined in turn to constitute a reverse wavy shape, and head and tail of the reverse wavy shape may be adjacent, thus constituting a reverse annular wave. If a radian of the concave shape at the top of each n-like shape is controlled, when multiple the n-like shapes are adjacent, the concave shapes of the n-like shapes may be combined in turn to constitute an approximate circle.

In an exemplary embodiment, the shape of the heater may be the same as the first shape.

In an exemplary embodiment, for example, the shape of the heater may include, but is not limited to, a symmetrical geometry, an annular sawtooth shape, an annular wave, or a circle, etc. For example, a heater including a heating part and a lead-out part is symmetrical geometry, wherein the heating part may be an annular sawtooth shape, an annular wave, or a circle, etc.

In an exemplary embodiment, when the strip-shaped heating electrode parts A321 in the N gas detection components A3 form the first shape accordingly with a combination of the first detection electrode segment A323-1-1 and the third detection electrode segment A323-2-1 in the N gas detection components A3, strip-shaped heating electrode parts A321 in any two adjacent gas detection components A3 of the N gas detection components A3 are connected to each other, thereby constituting a heater having a corresponding first shape of an approximate closed loop.

The shapes described in the exemplary embodiments herein such as the regular triangle, square, regular pentagon, hexagon, regular hexagon, m shape, n shape, M shape and the like refer to approximate shapes. For example, the regular triangle, square, regular pentagon and regular hexagon include an approximate regular triangle, an approximate square, an approximate regular pentagon and an approximate regular hexagon, it is not required that the side lengths are equal in a strict sense, and certain errors may be allowed.

Figure 13:
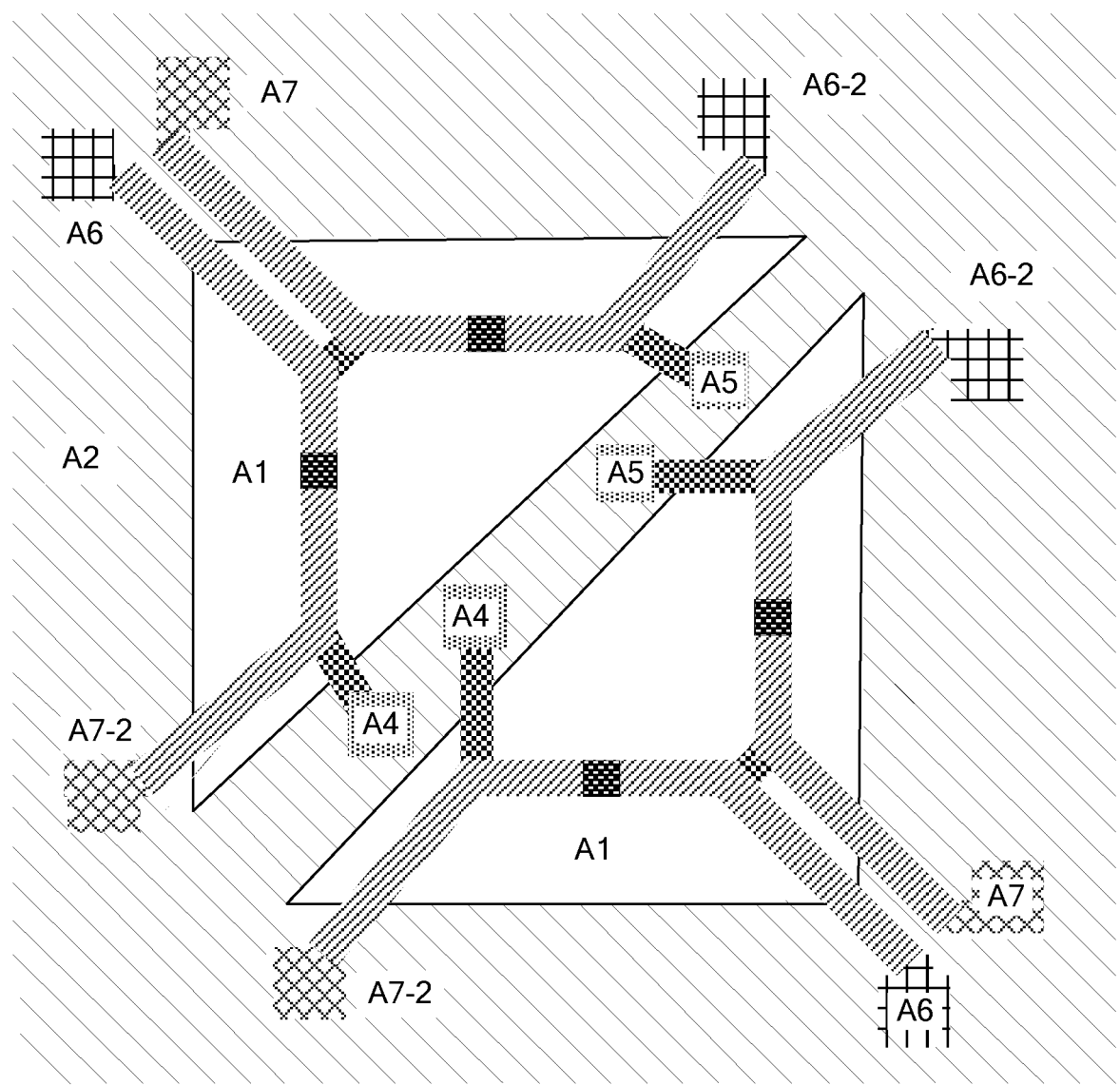
FIG. 13 is a schematic diagram of the first cavity being multiple first cavities according to an exemplary embodiment of the present disclosure.

In an exemplary embodiment, the first cavities A1 may be multiple, and FIG. 13 shows an embodiment including two first cavities A1. In FIG. 13, two gas detection components A3 are respectively provided at the opening of each cavity, the two gas detection components A3 are V-shaped, the strip-shaped heating electrode parts in the two gas detection components jointly constitute a V-shaped heater that is connected with two heating electrode pins. In this embodiment, the heater at each cavity opening has its own heating electrode pins, as shown in A4 and A5 in FIG. 13.

Figure 14:
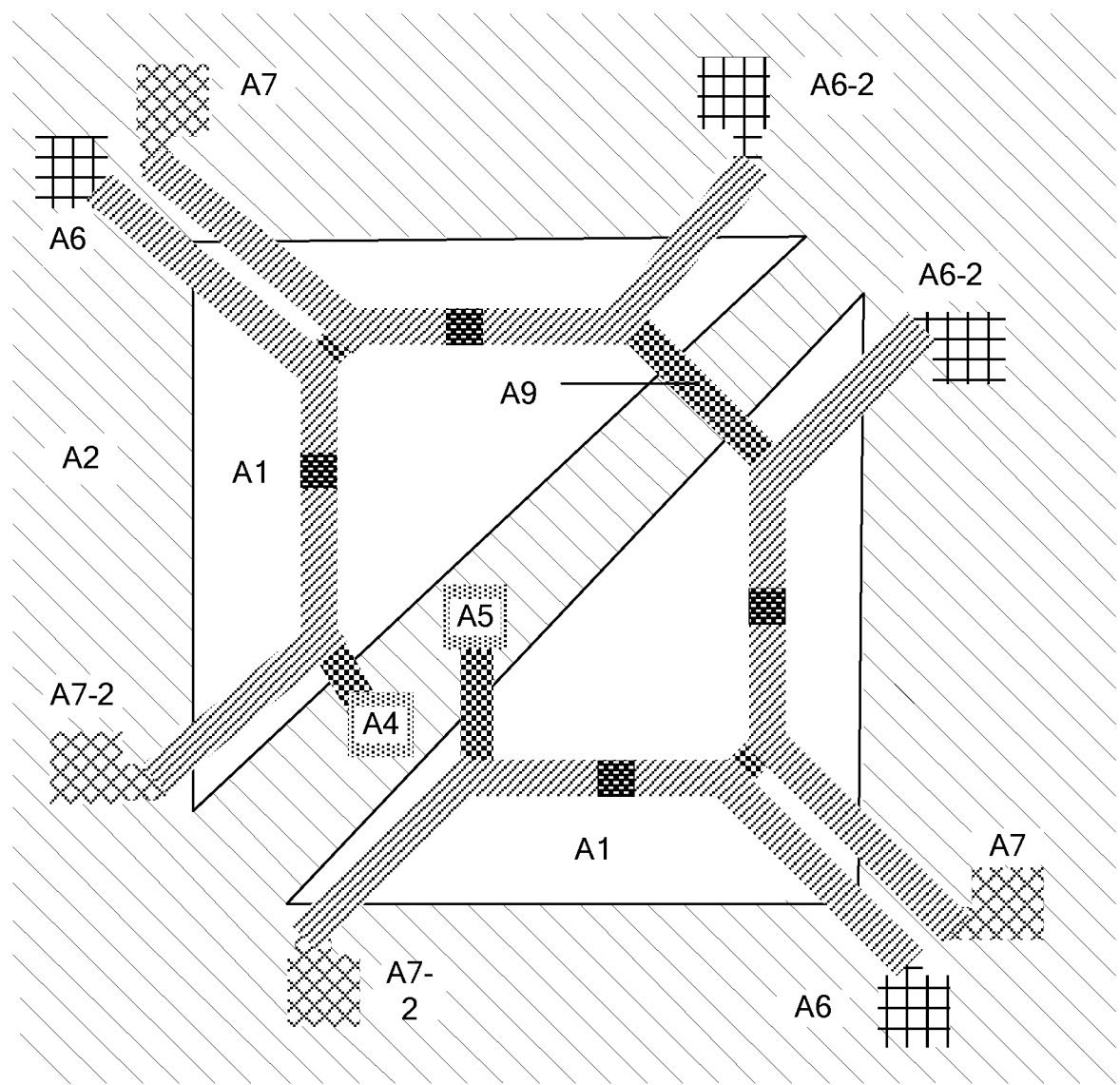
FIG. 14 is a schematic diagram of an overall heater constituted by multiple heaters at openings of multiple first cavities when there are multiple first cavities, according to an exemplary embodiment of the present disclosure.

In an exemplary embodiment, when there are multiple first cavities and each first cavity is provided with multiple gas detection components, heating electrode parts in the multiple gas detection components of the multiple cavities may share a heating electrode pin. As shown in FIG. 14, multiple heaters corresponding to the multiple first cavities A1 are connected to each other to constitute an overall heater A9.

It can be seen that all the gas detection components A3 provided at the opening of one first cavity A1 may share one heater, and when the first cavities A1 are multiple cavities, the heaters corresponding to the multiple first cavities A1 may be connected with each other to constitute an overall heater A9. The overall heater A9 may be shared by all the gas detection components A3 provided at the openings of the multiple first cavities A1. The shape of the overall heater A9 is a combined shape formed by the shapes of multiple heaters.

In an exemplary embodiment, in order to save space, the detection electrode pins may be shared. Two second detection electrode pins A7-2 shown in FIG. 14 may be merged into one pin to achieve pin sharing, and two first detection electrode pins A6-2 shown in FIG. 14 may be merged into one pin to achieve pin sharing.

In an exemplary embodiment, a first heating electrode pin A4 and a second heating electrode pin A5 of a heater A8 in a gas detection component at an opening of a first cavity A1 and a pair of first detection electrode pin A6 and second detection electrode pin A7 may be led out respectively by sharing a support arm (e.g. a segment, connected with a first substrate, of the support arm, such as a segment corresponding to the second detection electrode segment A323-1-2 and the fourth detection electrode segment A323-2-2 on the support arm having a bending point). Similarly, by sharing a support arm, the first heating electrode pin A4 and the second heating electrode pin A5 of the overall heater A9 at the openings of the multiple first cavities A1 and a pair of first detection electrode pin A6 and/or second detection electrode pin A7 at an opening of any one of the first cavities A1may be led out. Alternatively, by sharing a support arm, the first heating electrode pin A4 and the second heating electrode pin A5 of the overall heater A9 at the openings of the multiple first cavities A1 and any one first detection electrode pin A6 and any one second detection electrode pin A7 at the openings of any multiple first cavities A1may be led out the multiple.

According to the solution of the above-mentioned embodiments, the number of support arms formed in a process of manufacturing the gas sensor can be reduced, thereby simplifying the process.

In the following exemplary embodiments, an embodiment of a regular polygonal MEMS gas sensor is given. As mentioned above, the regular polygon described here includes the case of an approximate regular polygon.

In an exemplary embodiment, the regular polygonal MEMS gas sensor may include a first cavity A1; N (e.g., 6) gas detection components A3 may be provided at the opening of the first cavity A1. Accordingly, N support arms A31 may be provided, and each support arm A31 may be provided with a gas detection part A32.

In an exemplary embodiment, the support arm A31 is a part of a support film formed on the first substrate A2, that is, the support film is mounted at an area where the opening of the first cavity is located.

In an exemplary embodiment, the regular polygonal MEMS gas sensor may include N pairs of first detection electrode pins A6 and second detection electrode pins A7 corresponding to multiple strip-shaped detection electrode parts A323 in N gas detection parts A32. For example, for detection electrode parts on the six support arms A31 disposed at the opening of the first cavity A1, one pair of first detection electrode pin A6 and second detection electrode pin A7 are provided on the substrate for each detection electrode part, and the detection electrode part is connected, respectively, with the first detection electrode pin and the second detection electrode pin through detection electrode leads.

In an exemplary embodiment, N (e.g., 6) strip-shaped heating electrode parts A321 in the N (e.g., 6) gas detection parts A32 are connected sequentially to constitute one heater A8.

In an exemplary embodiment, there is only one heater A8 at the opening of one first cavity A1, the regular polygonal MEMS gas sensor may include a pair of first heating electrode pin A4 and second heating electrode pin A5 connected to the one heater A8, wherein the first heating electrode pin A4 and the second heating electrode pin A5 are connected, respectively, to two ends of the heater A8 through heating electrode leads.

In an exemplary embodiment, the first detection electrode part A323-1 in each strip-shaped detection electrode part A323 in a regular polygonal MEMS gas sensor may have a first bending point X1, and the second detection electrode part A323-2 in each strip-shaped detection electrode part A323 in the regular polygonal MEMS gas sensor may have a second bending point X2. The first detection electrode segment A323-1-1 and the third detection electrode segment A323-2-1 in each strip-shaped detection electrode part A323 may be disposed on a straight line (or an approximate straight line), and the first shape constituted by the first detection electrode segment A323-1-1 and the third detection electrode segment A323-2-1 in the N (e.g., 6) gas detection components A3 may be a regular polygon (or an approximate regular polygon), for example, a regular hexagon (which is open loop).

In an exemplary embodiment, the shape of the heater A8 in the regular polygonal MEMS gas sensor may be a closed-loop regular hexagon.

Figure 15:
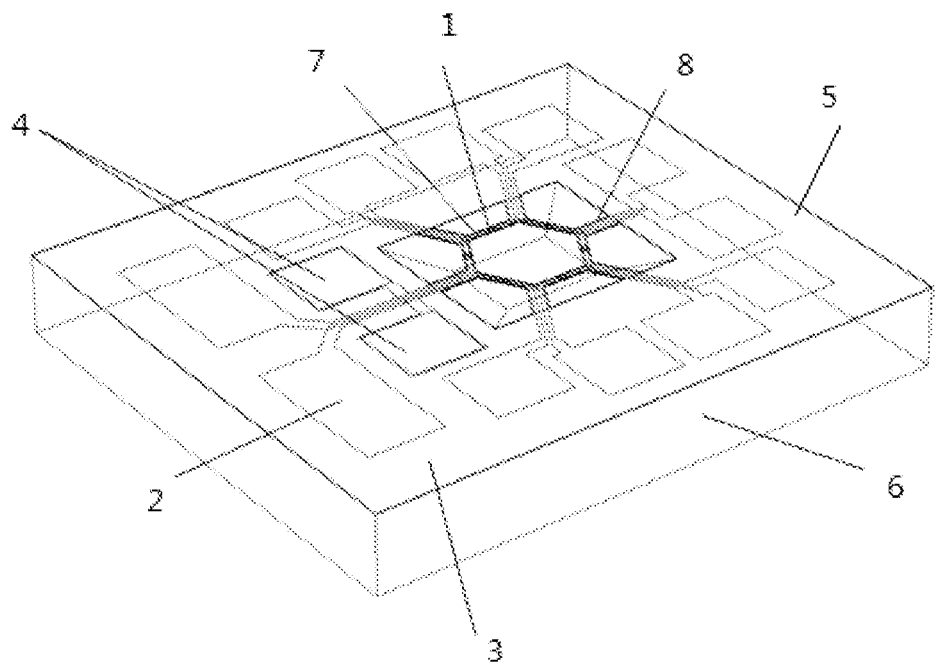
FIG. 15 is a perspective view of a structure of a regular polygonal MEMS gas sensor according to an exemplary embodiment of the present disclosure.

In an exemplary embodiment, as shown in FIG. 15, a regular polygonal MEMS gas sensor may include a gas sensitive material layer 1 (a layer where the gas sensitive material part A324 is located), a gas detection electrode layer 2 (a layer where the strip-shaped detection electrode part A323, the first detection electrode pin A6 and the second detection electrode pin A7 are located), an isolation film layer 3 (a layer where an insulating layer A322 between the strip-shaped heating electrode part A321 and a strip-shaped detection electrode part A323 is located), a heater layer 4 (a layer where the strip-shaped heating electrode part A321, the first heating electrode pin A4 and the second heating electrode pin A5 are located), a support film layer 5 (a layer where the support arm A31 is located), and a substrate layer 6 (a layer where the first substrate A2 is located).

In an exemplary embodiment, there are six effective gas sensors in the regular hexagonal MEMS gas sensor.

In this embodiment, the polygonal structure is employed, and slender sides are used as the sensitive parts of the gas sensors, which greatly reduces the power consumption. Since the six gas sensors share a closed-loop heater, five heaters can be reduced, so that heat taken away from the wire of the heater is reduced, and the power consumption can be reduced, the area occupied by the heater can be effectively reduced, which improves the integration level of the sensor.

In an exemplary embodiment, an area where the regular hexagonal MEMS gas sensor is located may be constituted by 6 sides 7 (i.e., 6 pairs of first detection electrode segments A323-1-1 and third detection electrode segments A323-2-1) and 6 beams 8 (i.e., 6 pairs of second detection electrode segments A323-1-2 and fourth detection electrode segments A323-2-2, and in this example, a pair of second detection electrode segments A323-1-2 and fourth detection electrode segments A323-2-2 share a beam) of the regular hexagon, and 6 sides 7 are supported by 6 beams 8 that connect 6 sides and a substrate (e.g., silicon substrate) to ensure stability of the structure. The support arm in the aforementioned embodiments includes the side and beam in this example.

In an exemplary embodiment, widths of the sides 7 and the beams 8 may be customized as required, which are not limited herein. For example, the width of each beam 8 may be 1.5 to 2.5 times the width of each side 7. For example, the width of each beam 8 may be twice the width of each side 7.

In an exemplary embodiment, the six gas detection parts A32 are disposed on the six sides 7, and by using the strip-shaped sides as the sensitive parts of the gas sensor, thermal mass is small and the power consumption is low.

In an exemplary embodiment, the regular hexagon has symmetry, which is the same as all regular polygons, so that the gas detection components are disposed on respective sides of the regular hexagon to ensure that temperature distribution of each of the gas detection components can be substantially consistent.

Figure 16:
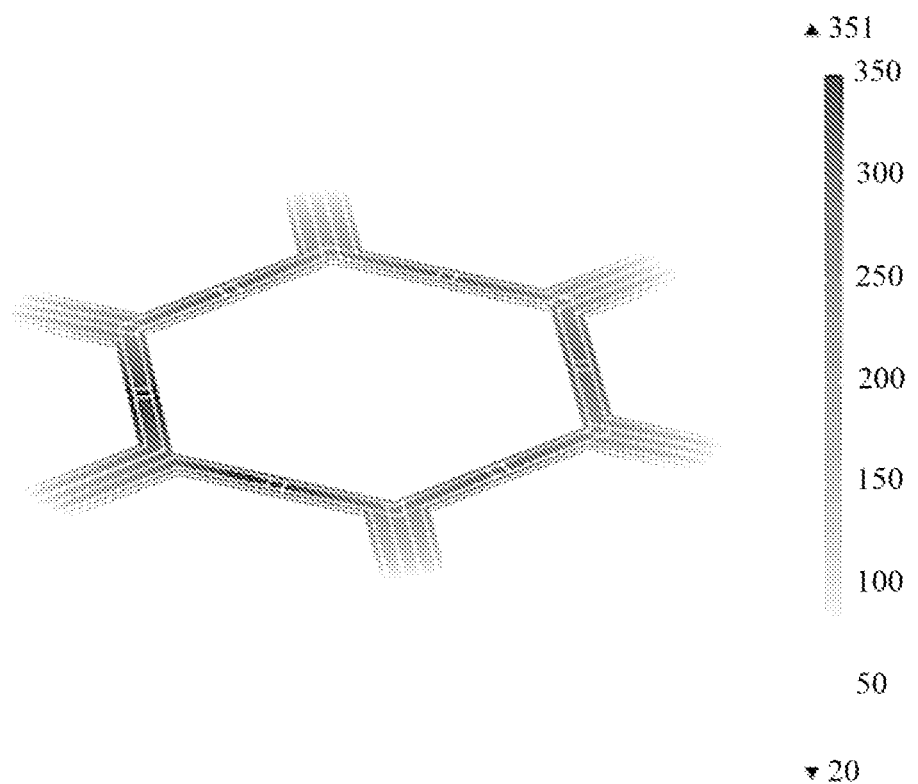
FIG. 16 is a schematic diagram of a simulation result of temperature distribution of a regular hexagonal gas sensor according to an exemplary embodiment of the present disclosure.

FIG. 16 shows a schematic diagram of a simulation result of temperature distribution of a regular hexagonal gas sensor. In FIG. 16, the closer to a black area, the higher the temperature. It can be seen that the high temperature area is a central area of each side.

Figure 18:
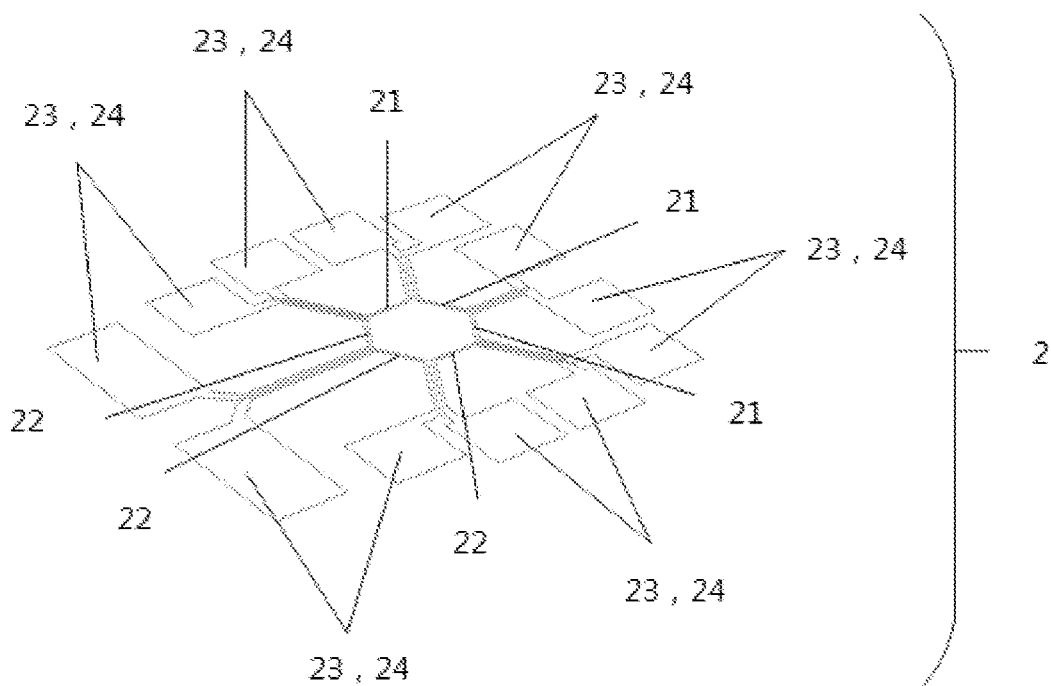
FIG. 18 is a schematic diagram of a gas detection electrode layer of a regular hexagonal MEMS gas sensor according to an exemplary embodiment of the present disclosure.

In an exemplary embodiment, both the gas sensitive material 11 and an electrode detection site 22 (i.e., the first opening A325) for placing the gas sensitive material 11 may be disposed in a middle area of each side 7. As shown in FIG. 18, the electrode detection site 22 may be disposed in the middle of each side 7.

In an exemplary embodiment, the gas sensitive material 11 may be covered on a position of the electrode detection site 22, for example, on the first opening A325 between the first detection electrode part and the second detection electrode part, or may be filled inside the first opening A325, as long as effective electrical connections are ensured with the first detection electrode part and the second detection electrode part, respectively.

Figure 17:
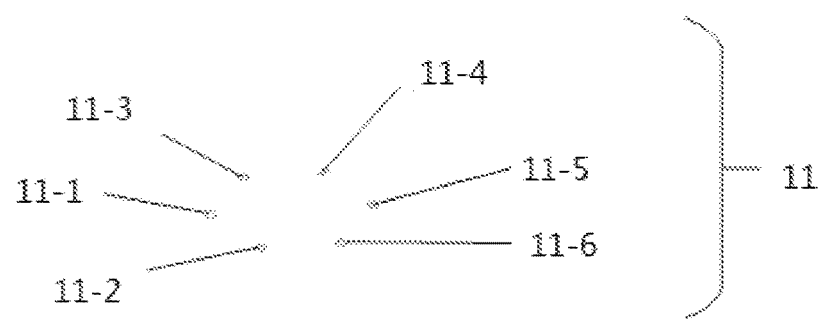
FIG. 17 is a schematic diagram of distribution of six gas sensitive materials of a regular hexagonal MEMS gas sensor according to an exemplary embodiment of the present disclosure.

FIG. 17 shows a distribution diagram of six gas sensitive materials 11-1, 11-2, 11-3, 11-4, 11-5 and 11-6 for the regular hexagonal gas sensor. The six gas sensitive materials may be the same material or different materials to form six gas sensors of the same or different kinds. In an exemplary embodiment, the kinds of the gas sensitive materials at the 6 sides may be different from each other; alternatively, the kinds of the gas sensitive materials at at least two sides are the same. When the kinds of the gas sensitive materials at the six sides differ from each other, there are equivalent to six kinds of gas sensors, which can be used to detect six different gases.

In an exemplary embodiment, when six gas detection components, which are provided with six different gas sensitive materials, are combined, more kinds of gases can be detected.

In an exemplary embodiment, six gas sensitive materials 11-1, 11-2, 11-3, 11-4, 11-5 and 11-6 of the regular hexagonal MEMS gas sensor may be the same material or different materials to form 6 gas sensors of the same or different kinds.

In an exemplary embodiment, the gas sensitive material 11 may include but is not limited to any one or more of the followings: tin oxide, indium oxide, tungsten oxide and zinc oxide.

As mentioned above, N sides may form N independent gas sensors of a same kind or different kinds, there are N effective discrete gas sensors on a regular N-sided gas sensor. By loading the same or different kinds of gas sensitive materials, it is easy to form an array of gas sensors of the same kind or different kinds, which is beneficial to the formation of an array of sensors and application of identification of various gases.

In an exemplary embodiment, as shown in FIG. 18, the gas detection electrode layer 2 is provided with a gas detection electrode 21 (i.e., the strip-shaped detection electrode part A323), an electrode detection site 22 (i.e., the first opening A235), a first electrode pin 23 (i.e., the first detection electrode pin A6), and a second electrode pin 24 (i.e., a second detection electrode pin A7). The first electrode pins 23 and the second electrode pins 24 are connected, directly or through the detection electrode leads, to the gas detection electrodes 21 each of which is electrically connected with the gas sensitive material 11 at an electrode detection site 22, thereby forming a gas detection circuit.

In the exemplary embodiment, the regular hexagonal MEMS gas sensor may include six gas detection components, and the shape of each gas detection component at the opening of a cavity may be shaped like a trapezoid, as shown in FIG. 4A. In other exemplary embodiments, as shown in FIGS. 2 and 3, a square MEMS gas sensor may be formed if four gas detection components are included, each of the gas detection components is shaped like an equilateral trapezoid in the figures. Strip-shaped detection electrode parts A323 are disposed at positions of an upper bottom and two sides of the equilateral trapezoid, and a gas sensitive material part A324 is provided at a first opening A325 (electrode detection site 22) at the upper bottom of the equilateral trapezoid.

Figure 19:
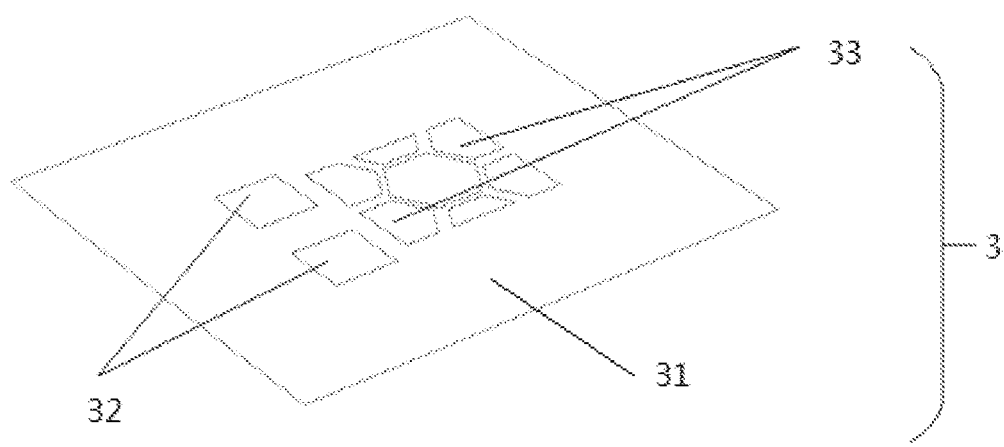
FIG. 19 is a schematic diagram of an isolation film layer of a regular hexagonal MEMS gas sensor according to an exemplary embodiment of the present disclosure.

FIG. 19 shows a schematic diagram of the isolation film layer 3 for isolating the gas detection electrode layer 2 from the heater layer 4. The isolation film layer 3 may be formed by a first isolation film 31, and the first isolation film 31 is provided with a first window 32 and a second window 33 to form the isolation film layer 3.

The first window 32 is configured to expose heating electrode pins of a heater 41.

The second window 33 is an etching window, which may be provided as, for example, a second shape formed by a vertical projection of hollow portions of multiple (e.g., six) equilateral trapezoidals on the isolation film layer 3, such as the area between six second windows 33 in FIG. 19. The shape may define the second window 33 when being vertically projected on the isolation film layer 3.

The cavity may be formed by, for example, wet etching through the second window 33 which is a wet etching window for releasing the first shape. The second window may include multiple sub-windows, the number of which depends on the number of gas detection components in the MEMS sensor and a shape combined by the gas detection components.

Figure 20:
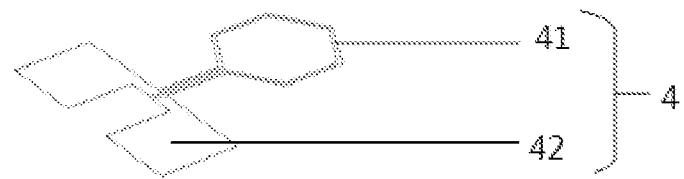
FIG. 20 is a schematic diagram of a heater layer of a regular hexagonal MEMS gas sensor according to an exemplary embodiment of the present disclosure.

In the exemplary embodiment, the heater layer 4 is provided with one heater component. As shown in FIG. 20, the heater component may include a heater 41 (i.e., the aforementioned heater A8) and heating electrodes 42 connected with both ends of the heater 41, and the heater 41 may be connected with the heating electrodes through heating electrode leads. The heater 41 may be an annular heater, and may be disposed at a position corresponding to a regular hexagonal structure.

In an exemplary embodiment, if a regular polygonal structure is adopted, the heater 41 may be a polygonal heater formed by slender metal wires, and heat is taken away by, on average, only one beam per gas detection part, so that overall power consumption is low.

Figure 21:
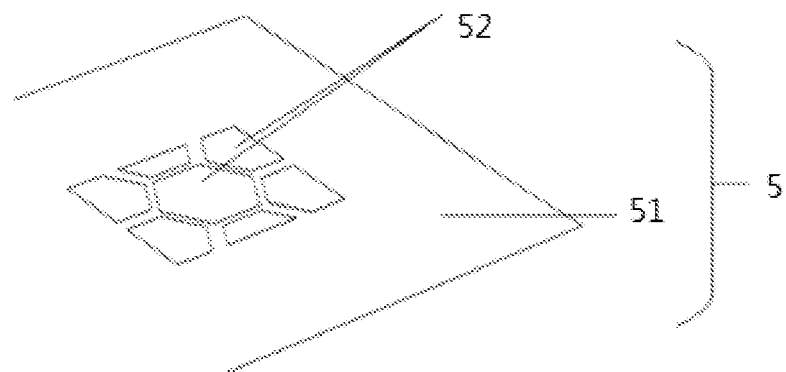
FIG. 21 is a schematic diagram of a support film layer of a regular hexagonal MEMS gas sensor according to an exemplary embodiment of the present disclosure.

In the exemplary embodiment, as shown in FIG. 21, the support film layer 5 may be formed by a second isolation film 51, and a third shaped body 52 may be released on the second isolation film 51 by, for example, etching, wherein the third shaped body 52 has the same shape as the second shape.

In the exemplary embodiment, the support film provided in the support film layer 5 is an isolation film (i.e., the second isolation film 51), and the third shaped body 52 is a wet etching window for etching to form a cavity.

Figure 22:
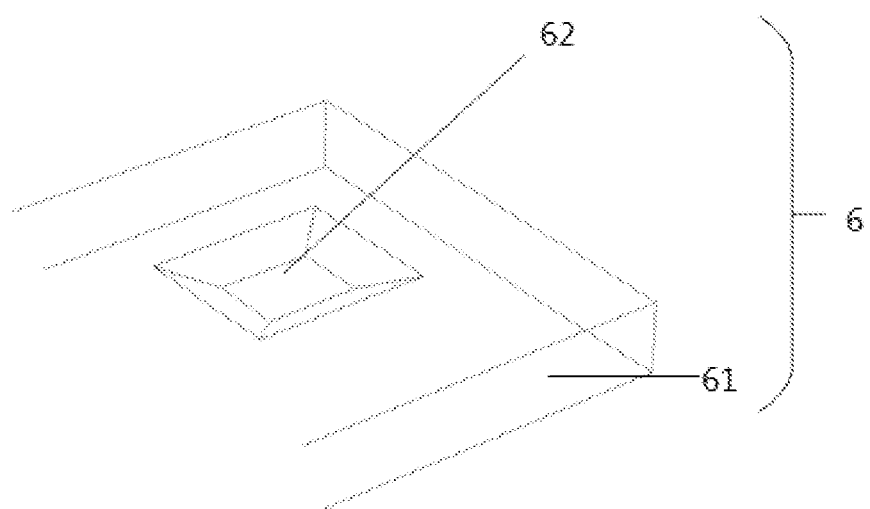
FIG. 22 is a schematic diagram of a substrate layer of a regular hexagonal MEMS gas sensor according to an exemplary embodiment of the present disclosure.

In an exemplary embodiment, as shown in FIG. 22, a substrate layer 6 may include a substrate 61 (i.e., the first substrate A2) provided with a hollow groove 62 (i.e., the first cavity A1), wherein the substrate 61 may be a silicon substrate with a <100> crystal orientation, and the hollow groove 62 may be a hollow groove formed by wet etching, for thermal insulation of the gas sensor.

In an exemplary embodiment, a shape of a structure of the hollow groove 62 may be, but is not limited to, a regular cylinder, an oblique cylinder, a regular truncated cone (cylinder with different areas of upper bottom surface and lower bottom surface, that is, a side surface is not perpendicular to the upper and lower bottom surfaces), an oblique truncated cone, a polyhedron (for example, cuboid, cube, regular hexahedron, etc.), an oblique polyhedron, a regular polyhedron, and a polygon (cylinder with different areas of upper bottom surface and lower bottom surface, that is, a side surface is not perpendicular to the upper and lower bottom surfaces), a regular polygon, an oblique polygon, a truncated cone with a side surface of an arbitrary curved surface, a truncated cone with an upper bottom surface and/or a lower bottom surface of an arbitrary shape, a truncated cone with a side surface of an arbitrary curved surface and an upper bottom surface and/or a lower bottom surface of an arbitrary shape, etc.

Figure 23:
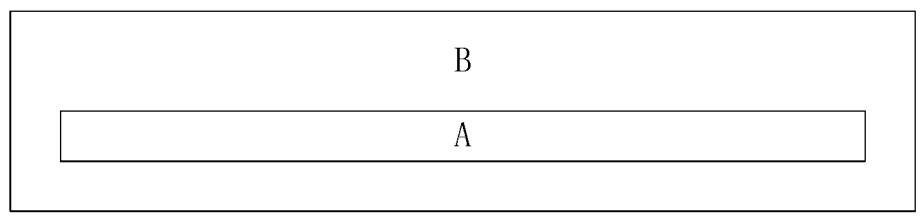
FIG. 23 is a schematic diagram of composition of an MEMS gas sensor array according to an exemplary embodiment of the present disclosure.

In another aspect, an MEMS gas sensor array B is further provided in an embodiment of the present disclosure, and as shown in FIG. 23, the MEMS gas sensor array B may include the MEMS gas sensor A of any of the above-mentioned embodiments.

In an exemplary embodiment, the gas sensor array B may include multiple gas sensors, wherein at least one gas sensor is an MEMS gas sensor as described in the above-mentioned embodiments.

For example, a gas sensor array B includes a total of five gas sensors, wherein two of the five gas sensors are MEMS gas sensors described in the embodiments of the present disclosure, or all of the five gas sensors are MEMS gas sensors described in the embodiments of the present disclosure. The above number of the gas sensors are for illustration only, therefore, there is no limitation herein on the number of MEMS gas sensors according to the embodiments of the present disclosure included in one gas sensor array B, and there is also no limitation herein on the distribution area, arrangement, connections with other gas sensors and the like of the included MEMS gas sensors according to the embodiments of the present disclosure.

Figure 24:
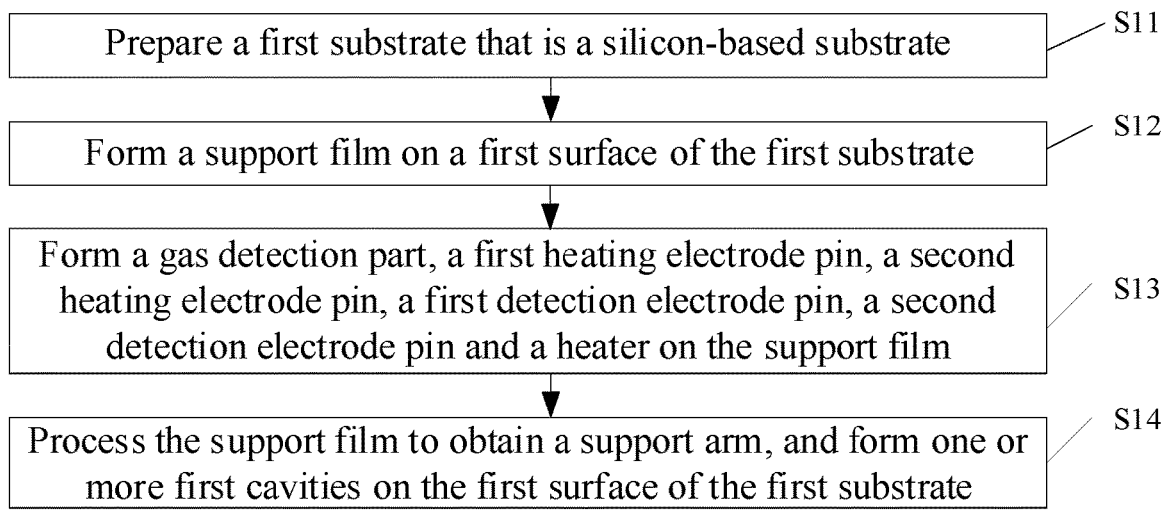
FIG. 24 is a flowchart of a method for manufacturing an MEMS gas sensor according to an exemplary embodiment of the present disclosure.

In yet another aspect, a method for manufacturing an MEMS gas sensor is further provided in an embodiment of the present disclosure, and the MEMS gas sensor may be the MEMS gas sensor described in any one of the above embodiments. As shown in FIG. 24, the method may include the following acts.

In S11, a first substrate is prepared.

In an exemplary embodiment, the first substrate may be, for example, a silicon-based substrate.

In S12, a support film is formed on a first surface of the first substrate.

In an exemplary embodiment, the forming the support film on the first surface of the first substrate may include: depositing a single-layer film or a composite film of a first silicon compound with a first preset thickness on the first surface of the first substrate as the support film.

For example, the film may be a silicon oxide film, a silicon nitride film, or a composite film composed of a silicon oxide layer and a silicon nitride layer, and may be a set of silicon oxide layer and silicon nitride layer or multiple sets of silicon oxide layers and silicon nitride layers.

In an exemplary embodiment, the method may further include: depositing a second silicon compound with a second preset thickness as a protective film on a second surface of the first substrate (e.g. a surface opposite to the first surface) after the support film is formed on the first surface of the first substrate.

In S13, a gas detection part, a first heating electrode pin, a second heating electrode pin, a first detection electrode pin, a second detection electrode pin and a heater are formed on the support film.

Figure 25:
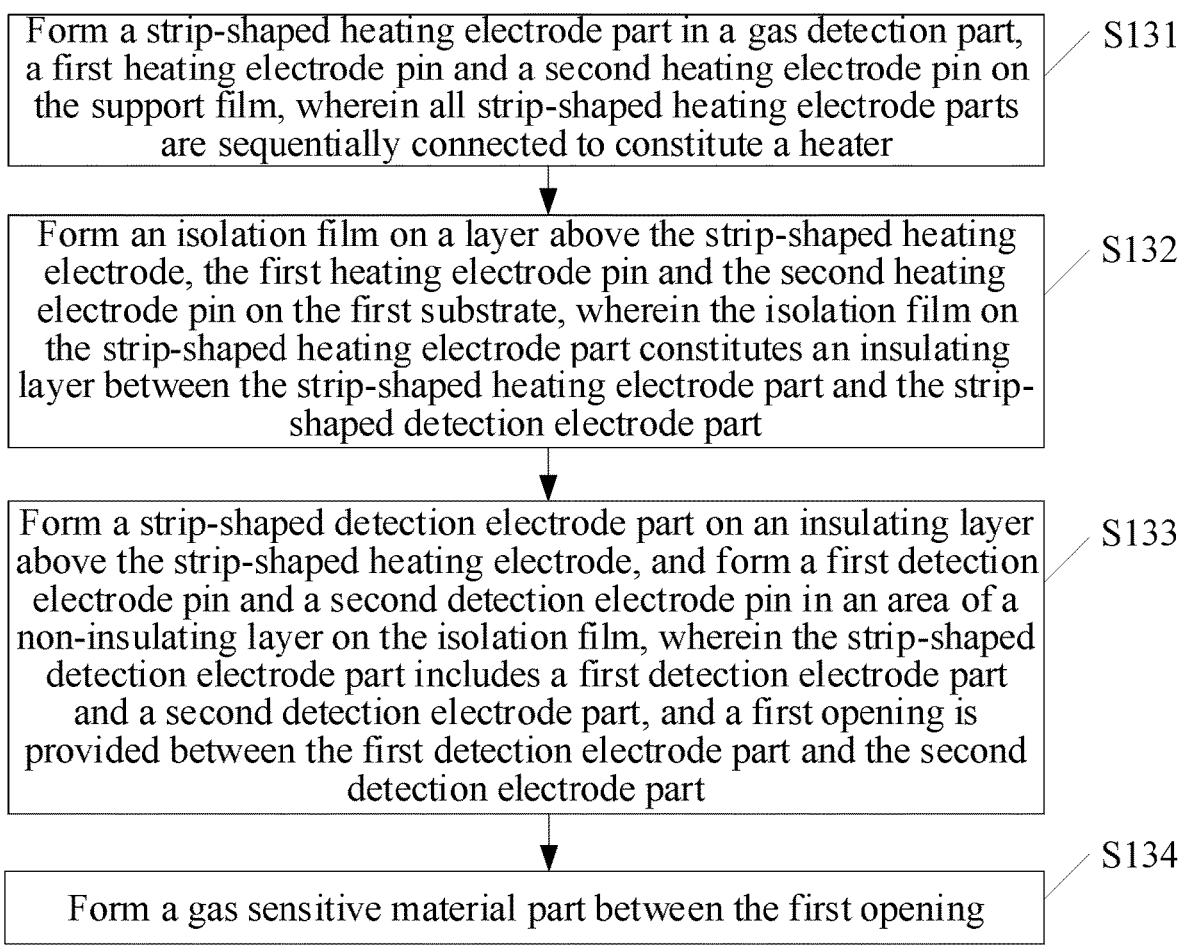
FIG. 25 is a flowchart of a method for manufacturing a gas detection part, a first heating electrode pin, a second heating electrode pin, a first detection electrode pin, and a second detection electrode pin on a support film according to an exemplary embodiment of the present disclosure.

In an exemplary embodiment, as shown in FIG. 25, the forming the gas detection part, the first heating electrode pin, the second heating electrode pin, the first detection electrode pin, and the second detection electrode pin on the support film may include acts S131 to S134.

In S131, a strip-shaped heating electrode part in a gas detection part, the first heating electrode pin and the second heating electrode pin are formed on the support film; wherein all strip-shaped heating electrode parts are sequentially connected to constitute a heater.

Alternatively, in an exemplary embodiment, leads may further be formed between the heating electrode part and the first heating electrode pin, and/or between the heating electrode part and the second heating electrode pin. Whether the lead is formed may be determined according to a distance between the heating electrode part and a pin.

In an exemplary embodiment, the act S131 may include: depositing a metal body with a third preset thickness as the strip-shaped heating electrode part in one or more first areas on the support film, and depositing a metal body with the third preset thickness as the first heating electrode pin and the second heating electrode pin in one or more second areas other than the first area; wherein, all of the strip-shaped heating electrode parts are sequentially connected to constitute a heater.

Alternatively, in an exemplary embodiment, leads may further be formed between the first heating electrode pin and the heating electrode part, and/or between the second heating electrode pin and the heating electrode part.

In S132, an isolation film is formed on a layer above the strip-shaped heating electrode, the first heating electrode pin and the second heating electrode pin on the first substrate; and the isolation film above the strip-shaped heating electrode part constitutes an insulating layer (strip-shaped insulating layer) between the strip-shaped heating electrode part and the strip-shaped detection electrode part.

The forming the isolation film on the layer above the strip-shaped heating electrode, the first heating electrode pin and the second heating electrode pin on the first substrate may include: depositing a third silicon compound with a fourth preset thickness as an isolation film on a layer above the strip-shaped heating electrode, the first heating electrode pin and the second heating electrode pin on the first substrate.

In S133, a strip-shaped detection electrode part is formed on an insulating layer above the strip-shaped heating electrode, and a first detection electrode pin and a second detection electrode pin are formed in an area of a non-insulating layer on the isolation film, wherein, the strip-shaped detection electrode part includes a first detection electrode part and a second detection electrode part, and a first opening is provided between the first detection electrode part and the second detection electrode part.

Alternatively, in an exemplary embodiment, leads may further be formed between the detection electrode pin and the detection electrode part, and/or between the second ground pin and the detection electrode part.

Forming the strip-shaped detection electrode part on the insulating layer above the strip-shaped heating electrode, and forming the first detection electrode pin and the second detection electrode pin in the area of the non-insulating layer on the isolation film may include: depositing an electrical conductor with a fifth preset thickness on a first portion of the insulating layer as the first strip-shaped detection electrode part, and depositing an electrical conductor with a fifth preset thickness on a second portion of the insulating layer as the second strip-shaped detection electrode part. Optionally, the first strip-shaped detection electrode part and the second strip-shaped detection electrode part may be deposited at the same time, wherein the insulating layer includes the first portion, the second portion, and a third portion, the third portion is located between the first portion and the second portion, and corresponds to the first opening.

In an exemplary embodiment, after the strip-shaped detection electrode part is formed on the insulating layer above the strip-shaped heating electrode, and the first detection electrode pin and the second detection electrode pin are formed in the area of the non-insulating layer on the isolation film, the method may further include: processing the isolation film above the first heating electrode pin and the second heating electrode pin to expose the first heating electrode pin and the second heating electrode pin. In an exemplary embodiment, the isolation film above the first and second heating electrode pins may be processed (etched) using a photolithography process and/or a dry etching process.

In S134, a gas sensitive material part is formed at the first opening.

The gas sensitive material part may be manufactured by a gas phase approach, a liquid phase approach or a solid phase approach. This act may also be made after the cavity is etched, i.e. an act S14.

In S14, the support film is processed to obtain a support arm, and one or more first cavities are formed on the first surface of the first substrate.

In an exemplary embodiment, processing the support film to obtain the support arm may include: releasing at least two hollow shapes on the support film using a dry etching process (e.g. reactive ion etching) to form the support arm (between the two hollow shapes).

In an exemplary embodiment, the forming one or more first cavities on the first surface of the first substrate may include: releasing the one or more first cavities with an anisotropic etching liquid of a preset compound on the first substrate.

For example, during etching, the cavity may penetrate through the first substrate, or, a depth of the cavity may be controlled so that a gap for thermal insulation is left between the gas detection component and the bottom of the cavity.

In an exemplary embodiment, during etching, the isolation film and the support film may be etched layer by layer at one time.

Figure 26:
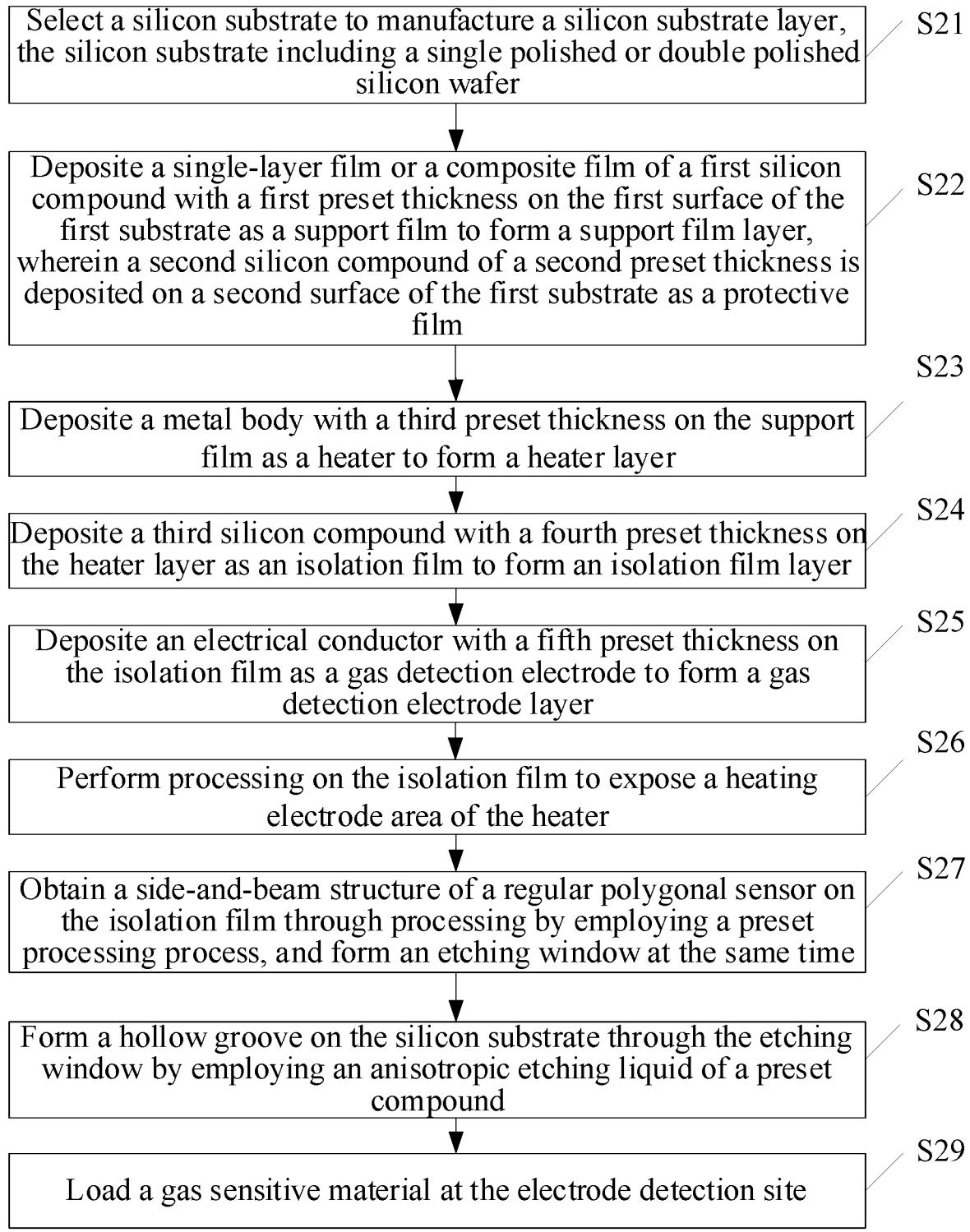
FIG. 26 is a flowchart of a method for manufacturing each layer of an MEMS gas sensor according to an exemplary embodiment of the present disclosure.

The above-mentioned method for manufacturing the MEMS gas sensor will be described below by an exemplary embodiment in which, as shown in FIG. 26, a silicon substrate layer, a support film layer, a heater layer, an isolation film layer, a gas detection electrode layer, and a gas sensitive material layer are sequentially manufactured, and the method may include acts S21 to S29.

In S21, a silicon substrate is selected to manufacture a first substrate, wherein the first substrate may include, but is not limited to, a silicon substrate layer, and the silicon substrate may include a single polished or double polished silicon wafer.

In this exemplary embodiment, a single polished or double polished silicon wafer with a <100> crystal orientation may be selected as the substrate.

In S22, a single-layer film or a composite film of a first silicon compound with a first preset thickness is deposited on the first surface of the first substrate as a support film to form a support film layer, wherein a second silicon compound of a second preset thickness is deposited on a second surface of the first substrate as a protective film.

In an exemplary embodiment, the first preset thickness may range from 1.5 microns to 2.5 microns, the first silicon compound may include a silicon oxide and/or a silicon nitride, the second preset thickness may range from 200 nm to 500 nm, and the second silicon compound may include a silicon nitride.

In the exemplary embodiment, the single-layer or composite film of the first silicon compound (such as silicon oxide and silicon nitride) may be deposited as the support film on a front surface of the silicon wafer (i.e., the above-mentioned first surface that is usually a polished surface, or it may be a non-polished surface) using Plasma Enhanced Chemical Vapor Deposition (PECVD) or Low Pressure Chemical Vapor Deposition (LPCVD), and a total thickness (i.e., the above-mentioned first preset thickness) may be 2 microns.

In an exemplary embodiment, a second silicon compound (e.g., silicon nitride) of 200 nm to 500 nm (the second preset thickness) may be deposited as a protective film of wet etching on a back surface of the silicon wafer (i.e., the above-mentioned second surface that is usually a non-polished surface, or it may be a polished surface) using PECVD or LPCVD.

The protective film may be provided on one or more surfaces of the first substrate.

In S23, a metal body with a third preset thickness is deposited on the support film as a heater to form a heater layer.

In an exemplary embodiment, the third preset thickness may range from 150 nm to 250 nm, and a material of the metal body may include platinum.

In an exemplary embodiment, a photolithography process and a metal coating process may be employed to deposit a metal body (e.g. platinum) with the third preset thickness (e.g., 200 nm) on the support film to form a heater layer.

The lithography process may be ultraviolet lithography, and the coating process may be electron beam evaporation coating or magnetron sputtering coating.

In S24, a third silicon compound with a fourth preset thickness is deposited on the heater layer as an isolation film to form an isolation film layer.

In an exemplary embodiment, the fourth preset thickness may range from 350 nm to 500 nm, and the third silicon compound may include silicon nitride.

In an exemplary embodiment, the third silicon compound (e.g. silicon nitride) with the fourth preset thickness (e.g., 350 nm to 500 nm) may be deposited as the isolation film using PECVD.

In S25, an electrical conductor with a fifth preset thickness is deposited on the isolation film as a gas detection electrode to form a gas detection electrode layer.

In an exemplary embodiment, the fifth preset thickness may range from 150 nm to 250 nm, and the metal body may include platinum or gold.

In an exemplary embodiment, the gas detection electrode layer may be manufactured using the process described in the act S133, i.e., an electrical conductor with a fifth preset thickness (e.g., 200 nm) is deposited on the isolation film as a detection electrode, and a material of the detection electrode may be platinum or gold.

In S26, processing is performed on the isolation film to expose a heating electrode pin area of the heater.

In an exemplary embodiment, a photolithography process and a dry etching process may be used to expose the heating electrode pin area of the heater. The dry etching process may be Reactive Ion Etching (RIE) or Inductively Coupled Plasma Etching (ICP-Etch).

In S27, a side-and-beam structure of a regular polygonal sensor is obtained on the isolation film through processing by employing a preset processing process, and an etching window is formed at the same time.

In an exemplary embodiment, the preset processing process may include a photolithography process and/or a dry etching process. That is, the side-and-beam structure of the regular polygonal MEMS gas sensor may be formed by employing a photolithography process and a dry etching process (RIE or ICP-Etch).

In S28, a hollow groove is formed on the silicon substrate through the etching window by employing an anisotropic etching liquid of a preset compound.

In an exemplary embodiment, the preset compound may include a potassium hydroxide (KOH) or tetramethyl ammonium hydroxide (TMAH) solution. In other words, the side-and-beam structure may be released by employing an anisotropic etching solution of silicon, such as potassium hydroxide or tetramethyl ammonium hydroxide solution, and the hollow groove may be formed on the silicon substrate at the same time.

In S29, a gas sensitive material is loaded at the electrode detection site.

In an exemplary embodiment, this act may be performed prior to the acts S27 or S28.

Semiconductor gas sensitive materials, such as tin oxide, indium oxide, tungsten oxide or zinc oxide, may be loaded at the electrode detection site.

The above descriptions are only embodiments of the present disclosure and are not intended to limit the protection scope of the present disclosure. Those of ordinary skills in the art should understand that modifications or equivalent replacements may be made to the technical solutions of the embodiments of the present disclosure without departing from the spirit and scope of the technical solutions of the embodiments of the present disclosure, and should all fall within the scope of the claims of the present disclosure.

The invention claimed is:

1. A Micro-Electro-Mechanical System (MEMS) gas sensor, comprising a first substrate with a first surface on which a first cavity is provided, N gas detection components disposed at an opening of the first cavity, wherein N is a positive integer greater than or equal to 2, wherein:
   each gas detection component comprises a support arm and a gas detection part disposed on the support arm; the gas detection part comprises a strip-shaped heating electrode part, an insulating layer, a strip-shaped detection electrode part and a gas sensitive material part, that are sequentially stacked; the strip-shaped detection electrode part comprises a first detection electrode part and a second detection electrode part, a first opening is provided between the first detection electrode part and the second detection electrode part, the gas sensitive material part is disposed at a position of the first opening, a first end of the gas sensitive material part is connected with the first detection electrode part, and a second end of the gas sensitive material part is connected with the second detection electrode part;
   strip-shaped heating electrode parts in all gas detection components are sequentially connected to form a heater; wherein the MEMS gas sensor further comprises:
   one or N first detection electrode pins and one or N second detection electrode pins, that are disposed on the first substrate, wherein
   a first end of one first detection electrode part is connected with a first end of one gas sensitive material part, a second end of the first detection electrode part is connected with one first detection electrode pin, and
   a first end of one second detection electrode part is connected with a second end of one gas sensitive material part, and a second end of the second detection electrode part is connected with one second detection electrode pin.

2. The MEMS gas sensor of claim 1, further comprising: a first heating electrode pin and a second heating electrode pin, that are disposed on the first substrate, wherein
   the first heating electrode pin is connected with a first end of the heater, and the second heating electrode pin is connected with a second end of the heater.

3. The MEMS gas sensor of claim 1, wherein
   the N gas detection components comprise N pairs of first detection electrode pins and second detection electrode pins, and
   the N pairs of first detection electrode pins and second detection electrode pins are connected with first detection electrode parts and second detection electrode parts in the N gas detection components, respectively.

4. The MEMS gas sensor of claim 1, wherein
   second ends of a plurality of first detection electrode parts are connected with one first detection electrode pin; and/or
   second ends of a plurality of second detection electrode parts are connected with one second detection electrode pin.

5. The MEMS gas sensor of claim 1, wherein the first detection electrode part and the second detection electrode part are symmetrical with each other, and the first opening is located at a position of a symmetry axis of the first detection electrode part and the second detection electrode part.

6. The MEMS gas sensor of claim 1, wherein the first detection electrode part in each gas detection component comprises a first bending point, and the first bending point divides the first detection electrode part into a first detection electrode segment and a second detection electrode segment;
   the second detection electrode part in each gas detection component comprises a second bending point, and the second bending point divides the second detection electrode part into a third detection electrode segment and a fourth detection electrode segment;
   one detection electrode part comprises the second detection electrode segment, the first detection electrode segment, the third detection electrode segment and the fourth detection electrode segment, that are connected sequentially, wherein, the first opening is disposed between the first detection electrode segment and the third detection electrode segment, and first detection electrode segments and third detection electrode segments in the N gas detection components jointly form a first shape, and the first shape is a symmetrical shape;
   the strip-shaped heating electrode part in each gas detection component is disposed in an area between the first bending point and the second bending point in the gas detection component.

7. The MEMS gas sensor of claim 6, wherein the first shape comprises a symmetrical geometry.

8. The MEMS gas sensor of claim 6, wherein a shape of the heater is the same as the first shape.

9. The MEMS gas sensor of claim 1, wherein there are a plurality of first cavities;
   heaters corresponding to the plurality of first cavities are connected with each other.

10. The MEMS gas sensor of claim 1, wherein the N gas sensitive material parts of the N gas detection components employ different gas sensitive materials from each other, or at least two gas sensitive material parts employ a same gas sensitive material.

11. The MEMS gas sensor of claim 1, wherein a shape of the heater is a symmetrical geometry.

12. A Micro-Electro-Mechanical System (MEMS) gas sensor array, comprising a plurality of MEMS gas sensors of claim 1.

13. A method for manufacturing a Micro-Electro-Mechanical System (MEMS) gas sensor, wherein the MEMS gas sensor is the MEMS gas sensor of claim 1, and the method comprises:
   preparing a first substrate;
   manufacturing N gas detection components on a first surface of the first substrate, wherein N is a positive integer greater than or equal to 2, and each gas detection component comprises a support arm and a gas detection part disposed on the support arm; the gas detection part comprises a strip-shaped heating electrode part, an insulating layer, a strip-shaped detection electrode part and a gas sensitive material part, that are sequentially stacked, the strip-shaped detection electrode part comprises a first detection electrode part and a second detection electrode part, a first opening is provided between the first detection electrode part and the second detection electrode part, the gas sensitive material part is disposed at a position of the first opening, a first end of the gas sensitive material part is connected with the first detection electrode part, and a second end of the gas sensitive material part is connected with the second detection electrode part; strip-shaped heating electrode parts in all gas detection components are sequentially connected to form a heater.

14. The MEMS gas sensor of claim 7, wherein a shape of the heater is the same as the first shape.

* * * * *